(12) United States Patent
Dreher

(10) Patent No.: US 9,326,930 B2
(45) Date of Patent: May 3, 2016

(54) CALCIUM SEQUESTRATION COMPOSITIONS AND METHODS OF TREATING SKIN PIGMENTATION DISORDERS AND CONDITIONS

(75) Inventor: Frank Dreher, San Francisco, CA (US)

(73) Assignee: NEOCUTIS S.A., Pully (CH)

( * ) Notice: Subject to any disclaimer, the term of this patent is extended or adjusted under 35 U.S.C. 154(b) by 403 days.

(21) Appl. No.: 12/688,107

(22) Filed: Jan. 15, 2010

(65) Prior Publication Data
US 2010/0189795 A1 Jul. 29, 2010

Related U.S. Application Data

(60) Provisional application No. 61/145,325, filed on Jan. 16, 2009.

(51) Int. Cl.
| | |
|---|---|
| A61K 8/55 | (2006.01) |
| C07F 9/11 | (2006.01) |
| A61K 31/661 | (2006.01) |
| A61K 9/14 | (2006.01) |
| A61P 17/00 | (2006.01) |
| A61Q 19/02 | (2006.01) |

(52) U.S. Cl.
CPC .. *A61K 8/55* (2013.01); *A61Q 19/02* (2013.01)

(58) Field of Classification Search
CPC .................................. A61K 8/55; A61Q 19/02
USPC ...................... 424/484, 59; 514/23, 53, 59, 60
See application file for complete search history.

(56) References Cited

U.S. PATENT DOCUMENTS

| | | | | |
|---|---|---|---|---|
| 4,868,168 | A * | 9/1989 | O'Laughlin et al. | 514/179 |
| 5,008,100 | A * | 4/1991 | Zecchino et al. | 424/59 |
| 6,168,798 | B1 * | 1/2001 | O'Halloran et al. | 424/401 |
| 7,078,022 | B2 | 7/2006 | Maniscalco | |
| 8,551,458 | B2 * | 10/2013 | Monello et al. | 424/62 |
| 2003/0053968 | A1 * | 3/2003 | Wortzman et al. | 424/62 |
| 2003/0118619 | A1 * | 6/2003 | Suares et al. | 424/401 |
| 2005/0019282 | A1 | 1/2005 | Rendon | |
| 2005/0249690 | A1 * | 11/2005 | Rojas-Wahl et al. | 424/70.12 |
| 2006/0008453 | A1 * | 1/2006 | Breton et al. | 424/93.45 |
| 2007/0003502 | A1 * | 1/2007 | Tanabe et al. | 424/70.13 |
| 2007/0196296 | A1 * | 8/2007 | Osborne et al. | 424/61 |
| 2008/0206155 | A1 * | 8/2008 | Tamarkin et al. | 424/44 |
| 2008/0247960 | A1 * | 10/2008 | Yuan | 424/43 |
| 2009/0068255 | A1 * | 3/2009 | Yu et al. | 424/450 |
| 2009/0117061 | A1 * | 5/2009 | Gross | 424/59 |
| 2009/0148391 | A1 * | 6/2009 | Schmaus et al. | 424/59 |

FOREIGN PATENT DOCUMENTS

| | | | | |
|---|---|---|---|---|
| CH | WO 2008/028631 | * | 3/2008 | .............. A61K 8/34 |
| EP | 0669126 A1 | | 8/1995 | |
| EP | 0948308 B1 | | 2/2004 | |
| JP | 2008-088113 | * | 4/2008 | .............. A61K 31/198 |
| WO | WO-02080864 A1 | | 10/2002 | |
| WO | WO-03061768 A2 | | 7/2003 | |
| WO | WO-2004105736 A1 | | 12/2004 | |
| WO | WO-2008009860 A2 | | 1/2008 | |

OTHER PUBLICATIONS

Sagar et al. (Current Oncology—vol. 13, No. 3 pp. 99-107, 2006).*
Abdel-Malek et al. "The Melanocortin 1 Receptor is the Principal Mediator of the Effects of Agouti Signaling Protein on Mammalian Melanocytes." *J. Cell Sci.* 114.5(2001):1019-1024.
Barsh et al. "Biochemical and Genetic Studies of Pigment-Type Switching." *Pigment Cell Res.* 13.Supp.8(2000):48-53.
Berger et al. "A Reappraisal of the 21-Day Cumulative Irritation Test in Man." *J. Toxicol.—Cutaneous and Ocular Toxicol.* 1.2(1982):109-115.
Buhse et al. "Topical Drug Classification." *Int. J. Pharm.* 295(2005):101-112.
Casañola-Martín et al. "Dragon Method for Finding Novel Tyrosinase Inhibitors: *Biosilico* Identification and Experimental In Vitro Assays." *J. Med. Chem.* 42(2007):1370-1381.
Holdiness. "A Review of Contact Dermatitis Associated with Transdermal Therapeutic Systems." *Contact Dermatitis.* 20.1(1989):3-9.
Ishikawa et al. "Combination of Amino Acids Reduces Pigmentation in B16F0 Melanoma Cells." *Biol. Pharm. Bull.* 30.4(2007):677-681.
Jordan et al. "Melanocortin Receptors and Antagonists Regulate Pigmentation and Body Weight." *Bioessays.* 20.8(1998):603-606.
Joshi et al. "Melanoctye-Keratinocyte Interaction Induces Calcium Signalling and Melanin Transfer to Keratinocytes." *Pigment Cell Res.* 20.5(2007):380-384.
Kimbrough-Green et al. "Topical Retinoic Acid (Tretinoin) for Melasma in Black Patients: A Vehicle Controlled Clinical Trial." *Arch. Dermatol.* 130.6(1994):727-733.
Lanman et al. "The Role of Human Patch Testing in a Product Development Program." Joint Conference on Cosmetic Sciences, The Toilet Goods Association, Washington, D.C., Apr. 21-23, 1968.
Pankovich et al. "Tyrosine Transport in a Human Melanoma Cell Line as a Basis for Selective Transport of Cytotoxic Analogues." *Biochem J.* 280(1991):721-725.
Potterf et al. "Characterization of a Melansomal Transport System in Murine Melanocytes Mediating Entry of the Melanogenic Substrate Tyrosine." *J. Biol. Chem.* 271.8(1996):4002-4008.
Shallreuter. "Advances in Melanocyte Basic Science Research." *Dermatol. Clin.* 25.3(2007):283-291.
Solano et al. "Hypopigmenting Agents: An Updated Review on Biological, Chemical and Clinical Aspects." *Pigment Cell Res.* 19.6(2006):550-571.
Voisey et al. "Agouti: From Mouse to Man, from Skin to Fat." *Pigment Cell Res.* 15.1(2002):10-18.
Wolff. "Regulation of Yellow Pigment Formation in Mice: A Historical Perspective." *Pigment Cell Res.* 16.1(2003):2-15.

* cited by examiner

*Primary Examiner* — Johann R Richter
*Assistant Examiner* — Anna Falkowitz
(74) *Attorney, Agent, or Firm* — Mintz, Levin, Cohn, Ferris, Glovsky and Popeo, P.C.

(57) ABSTRACT

The present invention provides compositions containing one or more calcium sequestration agents and methods for topical application of such compositions to the skin to treat skin pigmentation disorders, such as melasma, post-inflammatory hyperpigmentation, pigmentation changes due to skin aging, or any other skin conditions related with normal such as skin of color or abnormal pigmentation such as hypo- or hyper-pigmentation in humans.

23 Claims, 3 Drawing Sheets

| Immediately (*i.e.*, within approximately 5 minutes) after opening respective container and placing compositions onto inert surface exposed to ambient environmental conditions typically occurring at home | After 17 days exposure to ambient environmental conditions typically occurring at home |

CALCIUM SEQUESTRATION COMPOSITIONS AND METHODS OF TREATING SKIN PIGMENTATION DISORDERS AND CONDITIONS

RELATED APPLICATIONS

This application claims priority to U.S. Ser. No. 61/145,325, filed Jan. 16, 2009, which is herein incorporated by reference in its entirety.

FIELD OF THE INVENTION

The invention relates generally to compositions containing one or more calcium sequestration agents and methods for topical application to the skin to treat skin pigmentation disorders, such as melasma, post-inflammatory hyperpigmentation, pigmentation changes due to skin aging, or any other skin conditions related with normal such as skin of color or abnormal pigmentation such as hypo- or hyper-pigmentation in humans.

BACKGROUND OF THE INVENTION

In humans, skin color arises from a complex series of cellular processes that are carried out within a group of cells known as melanocytes. Melanocytes are located in the lower part of the epidermis and their function is to synthesize a pigment, melanin, which protects the body from the damaging effects of ultraviolet radiation. Melanin is a biopolymer originating from conversions of the amino acids phenylalanine or tyrosine.

The mechanism by which the skin pigment melanin is formed (melanin formation=melanogenesis) and skin ultimately gets its color (skin color=skin pigmentation) is a multi-step process and involves the following main steps:

1) Uptake (active transport via transporter) of amino acid precursors (L-tyrosine, L-phenylalanine) into melanocytes promoted by active transport mechanism
2) Conversion (turnover) of phenylalanine into tyrosine catalyzed by enzyme phenylalanine hydroxylase in melanocytes
3) Uptake (active transport via transporter) of amino acid precursors L-tyrosine into melanosomes located in melanocytes promoted by active transport mechanism
4) Conversion (turnover) of L-tyrosine into L-Dopa by enzyme tyrosinase in melanosome
5) Conversion (turnover) of L-Dopa into dopaquinone by enzyme tyrosinase in melanosome
6) Conversion (turnover) of dopaquinone into two different types of melanin called eumelanin (i.e., darker melanin) and phaeomelanin (i.e., lighter melanin) by various biochemical pathways in melanosome. The amount of each type of melanin determines the color and degree of pigmentation in a person's skin
7) Once melanin is produced, transfer of melanosome with melanin from melanocytes to keratinocytes (which are found in the upper layers of the epidermis) via the melanocyte dendrites.

In spite of the fact that the chemical and enzymatic basis of melanogenesis and skin pigmentation are rather well-documented, their regulation at the cellular and biochemical level is only partially understood. For instance, it is well known that the activity of tyrosinase is promoted by the action of alpha-melanocyte stimulating hormone (α-MSH) and UV rays. However, the processes of melanosome maturation and melanosome transfer into the keratinocyte are currently far less studied and not yet understood.

Typically, the more melanin is formed, the darker (or more tanned) the skin. However, melanogenesis and skin pigmentation can be disturbed or disorder, which may lead to undesirable pigmentation patterns. Examples of pigmentation disorders (i.e., disorders where pigmentation is disturbed or disordered) include age spots, liver spots, melasma, hyperpigmentation, etc. This has lead to research to find compounds that will inhibit melanogenesis and reduce skin pigmentation. One of the targets of this research is tyrosinase, the enzyme which catalyses the initial steps in the generation of melanin.

Skin pigmentation has been of concern to human beings for many years. In particular, the ability to remove hyperpigmentation (i.e., areas of darker skin color than the surrounding or adjacent, normal pigmented skin), such as found in age spots, freckles or aging skin generally, is of interest to individuals desiring a uniform skin color, skin complexion, or skin tone. In certain areas of the world, general body whitening is desirable.

There are also hypopigmentation (i.e., areas of less dark skin color than the surrounding or adjacent, normal pigmented skin) and hyperpigmentation disorders that are desirable to treat. Likewise, the ability to generate a tanned appearance without incurring photodamage due to solar radiation is important to many individuals.

Many methods proposed to accomplish depigmentation (i.e., reduction or limitation of skin pigmentation or skin color). For example, arbutin, kojic acid, hydroquinone, retinoids, and other chemical compounds have been used for depigmentation. Chemicals that allow depigmentation of skin are also called skin lighteners, skin brighteners, skin whiteners, skin bleachers or actives with skin lightening, skin brightening, skin whitening or skin bleaching properties.

Many of these previous examples were not acceptable or were of limited efficacy in treating skin pigmentation. Most of these compounds have been described to address only a few steps of the multiple steps leading to melanin formation and ultimately skin pigmentation, which may result their limited efficacy. For instance, most chemicals used for depigmentation are described as inhibitors of tyrosinase. Although tyrosinase production and activity is a key factor in melanin formation, melanogenesis is a multi-step process and involves other important and rate-limiting steps than tyrosinase catalyzed conversion of L-tyrosine and L-Dopa and Dopa-quinone. In addition, many of these compounds have been found to be irritating to the skin and, therefore, undesirable for use. Also, precise application of all these compounds may be necessary in order to achieve the desired result and to avoid distinct line of demarcation between the areas of skin to which such previous compositions have been applied.

Accordingly, there is a need for compositions which inhibit melanogenesis and reduce skin pigmentation by modulating one or more of the multiple steps involved in melanogenesis and skin pigmentation. At the same time, there is also a need for compositions that allow skin depigmentation without irritation. The compositions and methods of the present invention address these long felt needs in the art.

SUMMARY OF THE INVENTION

The present invention provides compositions containing at least one calcium sequestering or calcium binding agent for treating or ameliorating at least one symptom of a skin pigmentation disorder or condition, in a subject in need thereof. Preferably, the calcium sequestering or binding agent is a phosphate. More preferably, the phosphate is glycerophosphoric acid or a, non-calcium, salt thereof. Most preferably, the phosphate is sodium glycerophosphate. The calcium sequestering or binding agent is present in the composition in the amount of about 0.1% to about 25%. When the calcium sequestering or binding agent is phosphate it is preferably present in the composition in the amount of about 1% to about 5% by weight.

The compositions for treating or ameliorating at least one symptom of a skin pigmentation disorder or condition in a subject in need thereof can contain a calcium sequestering or binding agent and can further contain one or more of the following agents, which modulate or regulate at least one step of melanogenesis: L-alanine, glycine, L-isoleucine, L-leucine, hydroquinone, 4-(1-phenylethyl)1,3-benzenediol, arbutin, bearberry leaf extract, kojic acid, oxyresveratrol, gnetol, retinoic acid or retinol, melanosome transfer inhibitor, or α-MSH antagonist.

Also provided are compositions that include at least one additional agent selected from the group consisting of skin moisturization or skin rejuvenation agents. For example, the skin moisturization or skin rejuvenation agents may be ascorbic acid, vitamin E, jojoba oil, shea butter, human fibroblast lysate, retinoic acid, retinol, and/or any derivatives thereof.

The compositions for treating, or ameliorating at least one symptom of, a skin pigmentation disorder or condition, in a subject in need thereof, are formulated for topical administration. By way of non-limiting example, the compositions of the invention can be in the form of a solution, an oil-in-water emulsion, a water-in-oil emulsion, a gel, an ointment, a patch, a paste, a liquid, a foam, a mousse, a spray, an aerosol, a triple emulsion, a nanoemulsion, a microemulsion, a hydrogel, a jelly, a dispersion, a suspension, and/or a tape. The compositions are stable, substantially free of calcium, do not cause an acnegenic/comedogenic response, and/or produce only minor skin irritation upon administration.

Also provided herein are methods of treating or ameliorating a skin pigmentation disorder comprising administering an effective amount of any of the compositions of the invention to a patient suffering therefrom. For example, the skin pigmentation disorder can include, but is not limited to, melasma, post-inflammatory hyperpigmentation, pigmentation changes due to skin aging, age or liver spots, freckles, or any other skin conditions related with normal such as skin of color or abnormal pigmentation such as hypo- or hyper-pigmentation. Preferably, administration of the compound reduces skin pigmentation. The subject can be any mammal, preferably a human.

The invention also provides pharmaceutical formulations containing any of the compositions described herein and at least one pharmaceutically acceptable carrier. Similarly, the invention also provides cosmetic formulations containing any of the compositions described herein an at least one cosmetically acceptable carrier. In other embodiments, the invention provides kits including, in one or more containers, these pharmaceutical or cosmetic formulations. Those skilled in the art will recognize that such kits may optionally contain instructions for use of the pharmaceutical or cosmetic formulations in the treatment or amelioration of said skin pigmentation disorder or condition.

The invention also includes unit dosage forms containing therapeutically effective amounts of any of the compositions and/or pharmaceutical formulations described herein.

Any of the compositions or formulations described herein can be used in methods of reducing skin pigmentation in a patient by administering an effective amount of the composition and/or formulation to the patient. In such methods, the effective amount of the composition is administered topically to the patient.

Also provided are compositions for treating or ameliorating at least one symptom of a skin pigmentation disorder or condition that include 59.68% (by weight) water, 0.1% (by weight) disodium EDTA, 0.3% (by weight) xanthan gum, 0.3% (by weight) chlorphenesisn, 0.6% (by weight) phenoxyethanol, 0.5% (by weight) undecylenoyl phenylalanine, 3.00% (by weight) sodium glycerophosphate, 1.00% (by weight) leucine, 6.00% (by weight) cetearyl alcohol/ceteareth-20, 6.00% (by weight) glyceryl stearate, 3.00% (by weight) diisopropyl adipate, 3.00% (by weight) caprylyl methicone, 1.00% (by weight) dimethicone, 1.00% (by weight) simmondsia chinensis (jojoba) seed oil, 1.00% (by weight) butryospermum parkii shea butter), 0.2% (by weight) DL-alpha tocopheryl acetate, 1.92% (by weight) citric acid 50% solution, 4.00% (by weight) hydroquinone, 0.4% (by weight) sodium metabisulfite, 2.00% (by weight) glycerin, 0.5% (by weight) phenylethyl resorcinol, 0.5% (by weight) aminopropyl ascorbyl phosphate, and 4.00% (by weight) hydroxyethyl acrylate/sodium acryloyldimethyl taurate copolymer isohexadecane polysorbate 60. For example, such a composition can be formulated as a water-in-oil emulsion.

Finally, the invention further provides a composition for treating or ameliorating at least one symptom of a skin pigmentation disorder or condition containing 63.41% (by weight) water, 0.1% (by weight) disodium EDTA, 0.3% (by weight) xanthan gum, 0.3% (by weight) chlorphenesisn, 0.6% (by weight) phenoxyethanol, 0.5% (by weight) undecylenoyl phenylalanine, 3.00% (by weight) sodium glycerophosphate, 1.00% (by weight) leucine, 1.92% (by weight) citric acid 50% solution, 8.25% (by weight) cetearyl alcohol/ceteareth-20, 6.00% (by weight) glyceryl stearate, 5.00% (by weight) diisopropyl adipate, 3.00% (by weight) caprylyl methicone, 1.00% (by weight) dimethicone, 1.00% (by weight) simmondsia chinensis (jojoba) seed oil, 1.00% (by weight) butryospermum parkii shea butter), 0.2% (by weight) DL-alpha tocopheryl acetate, 2.00% (by weight) glycerin, 0.5% (by weight) phenylethyl resorcinol, 0.5% (by weight) aminopropyl ascorbyl phosphate, and 0.42% (by weight) hydroxyethyl acrylate/sodium acryloyldimethyl taurate copolymer/isohexadecane/polysorbate 60. For example, such a composition can be formulated as a water-in-oil emulsion.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description.

DETAILED DESCRIPTION

Figure 1:
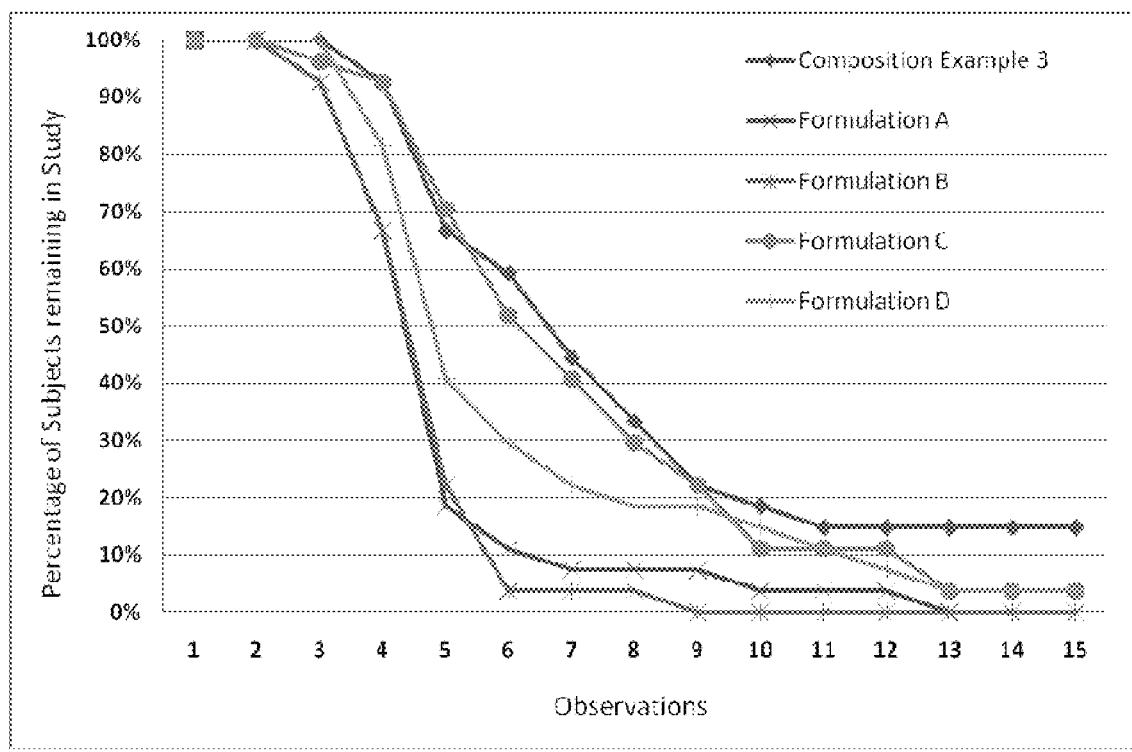
FIG. 1 is a graph showing skin irritation of a composition of the present invention (see Example 3, infra) as compared to other known compositions (e.g.: Compositions A to D), which are not part of this invention. This graph, which represents a "survival" type curve, shows the percentage of subjects who did not show any irritancy reaction reaching an evaluation score of "3" or higher as a function of time (i.e., observation) during the repetitive human irritancy patch test of three weeks (21 days) duration. As judged during this test (by providing "exaggerated" irritation data), the composition of the present invention was better tolerated (i.e., fewer subjects reached an evaluation score of "3" or higher with continued, prolonged application of patch with test material) as compared to Compositions A to D).

The present invention is directed to modulating (increasing or decreasing) various steps of melanogenesis (melanin formation) and to reduce skin pigmentation (skin color). More specifically, the present invention provides compositions for treating or ameliorating a symptom of a pigmentation disorder or condition involving a single active agent which modulates more than one step in the multi-step process of melanin formation and skin pigmentation. The present invention also provides compositions which contain at least two active agents (e.g., 2, 3, 4, 5, or more), where each active agent can target at least one step in the multi-step process of melanin formation. These multiple agents decrease melanin formation and skin pigmentation. By targeting multiple steps of melanogenesis and skin pigmentation, the compositions of present invention provide superior properties as compared to hypopigmentation products currently known in the art.

Calcium Sequestration or Binding Agents

Calcium ($Ca^{2+}$) may be an important regulator of some steps in melanogenesis and skin pigmentation. For instance, increase in calcium is believed to promote active transport of L-phenylalanine and its turnover via phenylalanine hydroxylase to L-tyrosine to significantly increase the pool of this substrate for melanogenesis. (See Dermatol Clin 25, 2007, pp. 283-291). Further, there is some evidence from in vitro studies that calcium impacts the melanosome transfer. (See Pigment Cell Res 20, 2007, pp. 380-384). This study, which used melanocyte-keratinocyte co-cultures, implied that melanin transfer was inhibited when intracellular calcium in keratinocytes was bound (chelated) with calcium chelator 1,2-bis-(o-aminophenoxy)-ethane-N,N,N',N'-tetraacetic acid tetraacetoxymethyl ester (BAPTA-AM).

Thus, the present invention provides compositions and methods for skin depigmentation which interferes one or more steps in the melanogenesis and skin pigmentation process where calcium is involved by administering a composition suitable for topical application containing at least one calcium sequestration or binding agent.

Examples of calcium sequestering or binding agents include either inorganic, organic (or a combination thereof, or organo-metallics) derived molecules. Preferably, the agents are calcium-free oxoanions of any or all possible oxidation states, achiral or chiral, selected from phosphates, phosphate esters, phosphonates, phosphonate esters, phosphoramidites, sulfates, sulfate esters, sulfonates, sulfonate esters, sulfites, siloxanes, carbonates, boronates, borinates, borinate esters, siloxanes, siloxane esters, polysiloxanes, sulfoxides, sulfonamides, sulfinic acids, sulfinimides, thiol esters, thioureas, and tosylates. Preferably the organic agents would possess calcium free anionic or neutral Lewis Base donors, achiral or chiral selected from carboxylic acids, polycarboxylates, carboxylic esters, nitriles, isocyanates, hydrazines, hydrazones, ureas, carboxylic esters, oximes, amides, amidines, thioethers, ethers, amines, alcohols, alkoxides, thiols, thiolates.

Table 1 recites non-limiting, representative, examples of carboxylic acids, boronic acids, amines, sulfates suitable to be utilized as calcium sequestration or binding agents

TABLE 1

| Product Code & Pack Size | | | Product Name | CAS | Structure | MF | MW |
|---|---|---|---|---|---|---|---|
| AC10430DA<br>AC10430EA | 1 GR<br>10 GR | 25.00 USD<br>189.00 USD | Amino-<br>phenylboronic<br>acid 0.5 ulfate | 66472-86-4 | 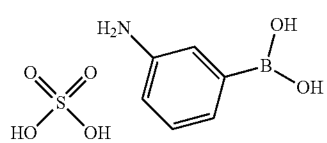 | $C6H8B\ NO2\cdot 0.5H2O4S$ | 185.98176<br>(136.94502) |
| AC10702EA<br>AC10702EE | 10 GR<br>50 GR | 19.00 USD<br>42.00 USD | 5-bromo-<br>2-furoic<br>acid | 585-70-6 | 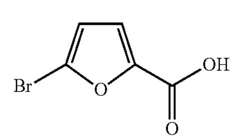 | $C5H3BrO3$ | 190.98102 |
| AC10728DA<br>AC10728EA | 1 GR<br>10 GR | 19.00 USD<br>102.00 USD | 4-<br>bromo-<br>phenylboronic<br>acid | 5467-74-3 | 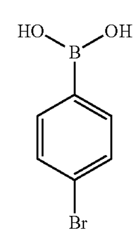 | $C6H6BBrO2$ | 200.82644 |

TABLE 1-continued

| Product Code & Pack Size | | | Product Name | CAS | Structure | MF | MW |
|---|---|---|---|---|---|---|---|
| AC11546EA<br>AC11546EE | 10 GR<br>50 GR | 21.00 USD<br>33.00 USD | 3,5-dimethoxy-benzoic acid | 1132-21-4 | 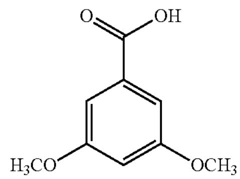 [SMILES: COc1cc(OC)cc(C(=O)O)c1] | C9H10O4 | 182.176 |
| AC11968DA | 1 GR | 59.00 USD | 2-amino-3-(5-fluoro-1H-indol-3-yl)propanoic acid | 154-08-5 | 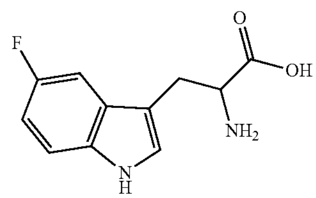 [SMILES: NC(Cc1c[nH]c2ccc(F)cc12)C(=O)O] | C11H11FN2O2 | 222.218943 |
| SEW01633CB<br>SEW01633DA<br>SEW01633DE | 250 MG<br>1 GR<br>5 GR | 93.00 USD<br>270.00 USD<br>761.00 USD | Thieno[2,3-b]thiophene-2-carboxylic acid | 14756-75-3 | 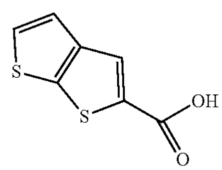 [SMILES: O=C(O)c1cc2ccsc2s1] | C7H4O2S2 | 184.22756 |
| AC12788DA<br>AC12788EA | 1 GR<br>10 GR | 48.00 USD<br>155.00 USD | 5-methyl-2-thiophene-carboxylic acid | 1918-79-2 | 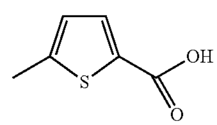 | C6H6O2S | 142.17244 |
| AC13036EA<br>AC13036EE | 10 GR<br>50 GR | 29.00 USD<br>117.00 USD | Phenylboronic acid | 98-80-6 | 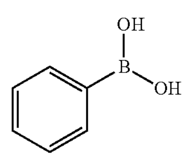 | C6H7BO2 | 121.93038 |
| AC13196EA | 10 GR | 74.00 USD | Pyridine-3-ylacetic acid hydrochloride | 6419-36-9 | 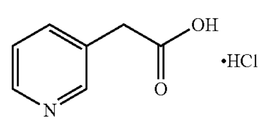 | C7H7NO2•HCl | 173.59902<br>(137.13808) |
| AC13366DA<br>AC13366EA | 1 GR<br>10 GR | 33.00 USD<br>65.00 USD | 2-piperazine-carboxylic acid dihydrochloride | 3022-15-9 | 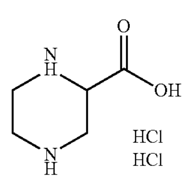 | C5H10N2O2•2 HCl | 203.06848<br>(130.1466) |
| AC14674CB<br>AC14674DA | 250 MG<br>1 GR | 179.00 USD<br>522.00 USD | 2-Amino-3-(6-fluoro-1H-indol-3-yl)-propanoic acid | 7730-20-3 | 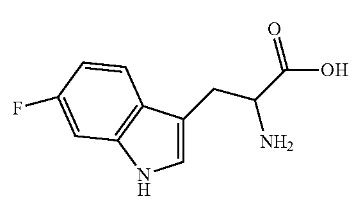 [SMILES: NC(Cc1c[nH]c2cc(F)ccc12)C(=O)O] | C11H11FN2O2 | 222.218943 |

Table 2 recites non-limiting, representative, examples of phosphates suitable to be utilized as calcium sequestration or binding agents.

TABLE 2

| Structure | Name |
|---|---|
| (1-naphthyl phosphate structure) | 1-Naphthyl phosphate |
| (2,4-diamino-6,7-diisopropylpteridine · H₃PO₄ structure) | 2,4-Diamino-6,7-diisopropyl-pteridine phosphate salt |
| (2-naphthyl phosphate disodium salt · xH₂O structure) | 2-Naphthyl phosphate disodium salt |
| (6-benzoyl-2-naphthyl phosphate disodium salt structure) | 6-Benzoyl-2-naphthyl phosphate disodium salt |

Table 3 recites non-limiting, representative, examples of phosphonates or phosphinates suitable to be utilized as calcium sequestration or binding agents.

TABLE 3

| Structure | Name |
|---|---|
| (ethyl methylphosphonate structure) | Ethyl methylphosphonate |
| (trimethyl phosphonoformate structure) | Trimethyl phosphonoformate |
| (diethyl cyanophosphonate structure) | Diethyl cyanophosphonate |

TABLE 3-continued

| Structure | Name |
|---|---|
| (O,O'-diethyl methylphosphonothioate structure) | O,O'-Diethyl methylphosphonothioate |
| (triethyl phosphonoformate structure) | Triethyl phosphonoformate |

Table 4 recites non-limiting, representative, examples of phosphonic/phosphoric acids suitable to be utilized as calcium sequestration or binding agents.

TABLE 4

| Structure | Name |
|---|---|
| (methylphosphonic acid structure) | Methylphosphonic acid |
| (aminomethylphosphonic acid structure) | (Aminomethyl)phosphonic acid |
| (methylenediphosphonic acid structure) | Methylenediphosphonic acid |
| (phosphonoacetic acid structure) | Phosphonoacetic acid |
| (dimethylphosphinic acid structure) | Dimethylphosphinic acid |
| (ethylphosphonic acid structure) | Ethylphosphonic acid |
| (2-aminoethylphosphonic acid structure) | 2-Aminoethylphosphonic acid |

Table 5 recites non-limiting, representative, examples of boronic acids suitable to be utilized as calcium sequestration or binding agents.

TABLE 5

| Product Code & Pack Size | | | Product Name | CAS | Structure | MF | MW |
|---|---|---|---|---|---|---|---|
| AC10430DA<br>AC10430EA | 1<br>GR<br>10<br>GR | 25.00<br>USD<br>189.00<br>USD | 3-amino-phenylboronic acid 0.5 sulfate | 66472-86-4 | 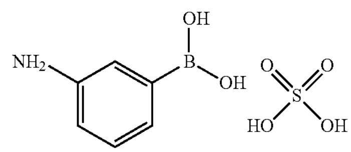 | C6H8B NO2•0.5H2O4S | 185.98176<br>(136.94502) |
| AC10728DA<br>AC10728EA | 1<br>GR<br>10<br>GR | 19.00<br>USD<br>102.00<br>USD | 4-bromo-phenylboronic acid | 5467-74-3 | 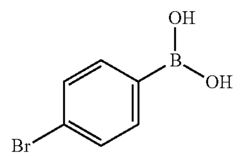 | C6H6BBrO2 | 200.82644 |
| AC13036EA<br>AC13036EE | 10<br>GR<br>50<br>GR | 29.00<br>USD<br>117.00<br>USD | Phenylboronic acid | 98-80-6 | 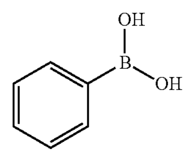 | C6H7BO2 | 121.93038 |
| AC30926DA<br>AC30926EA | 1<br>GR<br>10<br>GR | 19.00<br>USD<br>157.00<br>USD | 2-methylphenyl-boronic acid | 16419-60-6 | 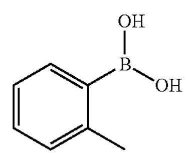 | C7H9BO2 | 135.95726 |
| AC30948DA<br>AC30948EA | 1<br>GR<br>10<br>GR | 81.00<br>USD<br>430.00<br>USD | 4-methoxy-phenyl-boronic acid | 5720-07-0 | 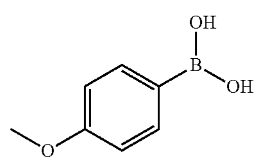 | C7H9BO3 | 151.95666 |
| AC34441DA<br>AC34441EA<br>AC34441EE | 1<br>GR<br>10<br>GR<br>50<br>GR | 48.00<br>USD<br>155.00<br>USD<br>577.00<br>USD | 4-chloro-phenylboronic acid | 1679-18-1 | 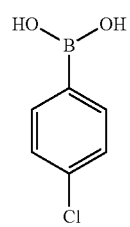 | C6H6BClO2 | 156.37544 |
| AC34443DA | 1<br>GR | 25.00<br>USD | 4-methyl-phenylboronic acid | 5720-05-8 | 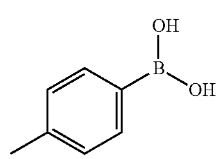 | C7H9BO2 | 135.95726 |
| AC34465DA<br>AC34465EA | 1<br>GR<br>10<br>GR | 33.00<br>USD<br>187.00<br>USD | Hexyl-boronic acid | 16343-08-1 | 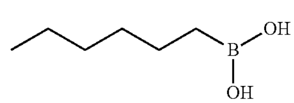 | C6H15 BO2 | 129.9939 |
| AC34468DA<br>AC34468EA | 1<br>GR<br>10<br>GR | 19.00<br>USD<br>117.00<br>USD | 4-(methylsulfa-nyl)phenyl-boronic acid | 98546-51-1 | 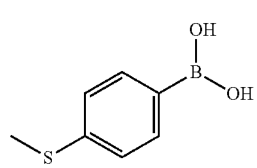 | C7H9BO2S | 168.01726 |

TABLE 5-continued

| Product Code & Pack Size | | | Product Name | CAS | Structure | MF | MW |
|---|---|---|---|---|---|---|---|
| AC34469DA AC34469EA | 1 GR 10 GR | 19.00 USD 151.00 USD | 1-naphthyl-boronic acid | 13922-41-3 | | C10H9BO2 | 171.99026 |
| AC35883DA AC35883EA | 1 GR 10 GR | 19.00 USD 151.00 USD | 3-acetyl-phenyl-boronic acid | 204841-19-0 | | C8H9BO3 | 163.96766 |

Table 6 recites non-limiting, representative, examples of esters or alcohols suitable to be utilized as calcium sequestration or binding agents.

TABLE 6

| Product Code & Pack Size | | | Product Name | CAS | Structure | MF | MW |
|---|---|---|---|---|---|---|---|
| CC03622DA | 1 GR | 102.00 USD | 1-Methyl-1H-imidazole-4-carboxylic acid methyl ester | 17289-19-9 | | C6H8N2O2 | 140.14172 |
| CC04940DA | 1 GR | 106.00 USD | Isoquinaline-4-boronic acid 2,2-dimethyl-propanedial-1,3 cyclic ester | 844891-01-6 | | C14H16 BNO2 | 241.09654 |
| CC19422DA | 1 GR | 159.00 USD | 3-(2-Methyl-thiazol-4-yl)-benzoic acid methyl ester | 850375-07-4 | | C12H11 NO2S | 233.28484 |
| MO07248CB MO07248DA | 250 MG 1 GR | 78.00 USD 161.00 USD | 3-(5-Bromo-pyridin-3-yl)-[1,2,4]oxa-diazole-5-carboxylic acid ethyl ester | 850375-37-7 | | C10H8BrN3O3 | 298.09582 |
| MO07285DA MO07285EA | 1 GR 10 GR | 66.00 USD 471.00 USD | (4-Hydroxy-methyl-benzyl)-carbamic acid tert-butyl ester | 123986-64-1 | | C13 H19NO3 | 237.29876 |

TABLE 6-continued

| Product Code & Pack Size | | | Product Name | CAS | Structure | MF | MW |
|---|---|---|---|---|---|---|---|
| MO07286CB<br>MO07286DA<br>MO07286DE | 250<br>MG<br>1<br>GR<br>5<br>GR | 78.00<br>USD<br>200.00<br>USD<br>546.00<br>USD | (3-Hydroxy-methyl-benzyl)-carbamic acid tert-butyl ester | 226070-69-5 | 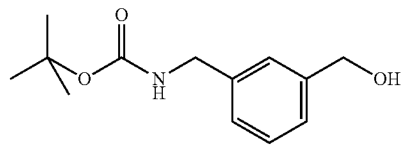 [SMILES: CC(C)(C)OC(=O)NCc1cccc(CO)c1] | C13H19 NO3 | 237.29876 |
| MO07352CB<br>MO07352DA<br>MO07352EA | 250<br>MG<br>1<br>GR<br>10<br>GR | 48.00<br>USD<br>95.00<br>USD<br>706.00<br>USD | 3-Amino-methylbenzo-ic acid methyl ester hydrochloride | 17841-68-8 | 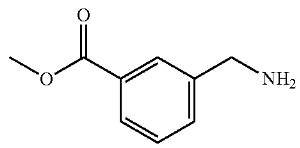 | C9H11 NO2•HCl | 201.65278<br>(165.19184) |
| RDP00077DA<br>RDP00077EA<br>RDP00077EB | 1<br>GR<br>10<br>GR<br>25<br>GR | 42.00<br>USD<br>65.00<br>USD<br>115.00<br>USD | (S)-tryptophan ethyl ester hydrochloride | 7479-05-2 | 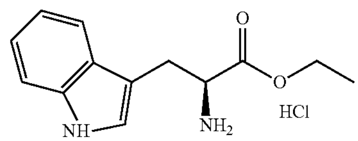 [SMILES: CCOC(=O)[C@@H](N)Cc1c[nH]c2ccccc12 ; Cl] | C13H16N2O2•ClH | 268.74318<br>(232.28224) |
| BTB06937EE<br>BTB06937FA | 50<br>GR<br>100<br>GR | 36.00<br>USD<br>65.00<br>USD | 4-methoxy-4-oxobutanoic acid | 3878-55-5 | 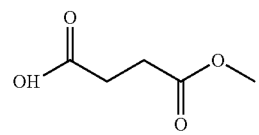 | C5H8O4 | 132.11612 |
| SB01817EE<br>SB01817FA | 10<br>GR<br>25<br>GR | 55.00<br>USD<br>83.00<br>USD | Methyl propiolate | 922-67-8 | 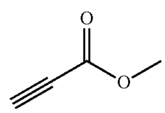 | C4H4O2 | 84.07456 |

Table 7 recites non-limiting, representative, examples of oximes suitable to be utilized as calcium sequestration or binding agents.

TABLE 7

| Product Code & Pack Size | | | Product Name | CAS | Structure | MF | MW |
|---|---|---|---|---|---|---|---|
| CD11194DA<br>CD11194EA | 1<br>GR<br>10<br>GR | 81.00<br>USD<br>432.00<br>USD | Azepan-2-one axime | 19214-08-5 | 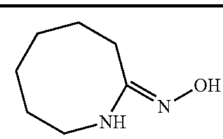 | C6H12N2O | 128.17408 |
| SPB04865DA<br>SPB04865EA<br>SPB04865EB | 1<br>GR<br>10<br>GR<br>25<br>GR | 51.00<br>USD<br>76.00<br>USD<br>142.00<br>USD | 2,4-dichlorobenz-aldehyde oxime | 56843-28-8 | 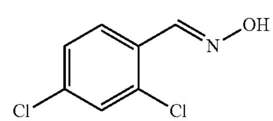 [SMILES: O/N=C/c1ccc(Cl)cc1Cl] | C7H5Cl2NO | 190.0288 |
| SPB04935EA<br>SPB04935FA | 10<br>GR<br>100<br>GR | 321.00<br>USD<br>801.00<br>USD | 3,4-dichlorobenz-aldehyde oxime | 5331-92-0 | 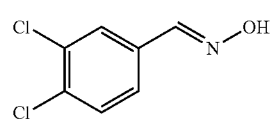 [SMILES: O/N=C/c1ccc(Cl)c(Cl)c1] | C7H5Cl2NO | 190.0288 |
| CD00359DA<br>CD00359EA<br>CD00359EE | 1<br>GR<br>10<br>GR<br>50<br>GR | 42.00<br>USD<br>65.00<br>USD<br>232.00<br>USD | 2-furaldehyde oxime | 1121-47-7 | 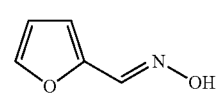 | C5H5NO2 | 111.1002 |
| SPB05555DA<br>SPB05555EA | 1<br>GR<br>10<br>GR | 55.00<br>USD<br>332.00<br>USD | 4-(trifluoro-methoxy)benz-aldehyde oxime | 150162-39-3 | 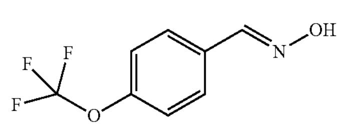 [SMILES: O/N=C/c1ccc(OC(F)(F)F)cc1] | C8H6F3NO2 | 205.13634 |

TABLE 7-continued

| Product Code & Pack Size | | | Product Name | CAS | Structure | MF | MW |
|---|---|---|---|---|---|---|---|
| SPB05820DA SPB05820EA SPB05820EE | 1 GR 10 GR 50 GR | 42.00 USD 65.00 USD 232.00 USD | 2,6-dichlorobenz-aldehyde oxime | 25185-95-9 | | C7H5Cl2NO | 190.0288 |
| END00218DA | 1 GR | 53.00 USD | 4-phenylbut-3-en-2-one oxime | 2887-98-1 | | C10H11NO | 161.20344 |
| SPB08294DA SPB08294EA SPB08294EB | 1 GR 10 GR 25 GR | 19.00 USD 147.00 USD 275.00 USD | 2-chloro-5-fluorobenz-aldehyde oxime | 443-33-4 | | C7H5ClFNO | 173.574203 |
| SPB08414DA SPB08414EA | 1 GR 10 GR | 53.00 USD 321.00 USD | 3,5-dibromo-4-hydrobenz-aldehyde oxime | 25952-74-3 | | C7H5Br2NO2 | 294.9302 |
| MO00284CB MO00284DA | 250 MG 1 GR | 68.00 USD 134.00 USD | 2-bromo-1-phenyl-1-ethanone oxime | 14181-72-7 | | C8H8BrNO | 214.06162 |
| KM08088DA | 1 GR | 53.00 USD | 4-(3-hydroxy-3-methylbut-1-yn-yl)benz-aldehyde oxime | 175203-57-3 | | C12H13NO2 | 203.24072 |
| TL00712DA TL00712EA TL00712EB | 1 GR 10 GR 25 GR | 57.00 USD 337.00 USD 426.00 USD | (1E)-1-(5,6,7,8-tetrahydro-naphthalen-2-yl) ethanone oxime | 7357-12-2 | | C12H15NO | 189.2572 |
| BTB09548DA BTB09548EA BTB09548EB | 1 GR 10 GR 25 GR | 29.00 USD 65.00 USD 81.00 USD | 3-phenylacryl-aldehyde oxime | 13372-81-1 | | C9H9NO | 147.17656 |

Table 8 recites non-limiting, representative, examples of sulfites suitable to be utilized as calcium sequestration or binding agents.

TABLE 8

| Product Code & Pack Size | | | Product Name | CAS | Structure | MF | MW |
|---|---|---|---|---|---|---|---|
| AC27651DA | 1 GR | 70.00 USD | 1-methyl-1H-benzimidazole-2-sulfonic acid | 5533-38-0 | 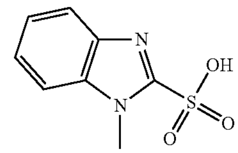 | C8H8N2O3S | 212.223312 |
| AC40114CA AC40114CB | 100 MG 250 MG | 74.00 USD 255.00 USD | Ammonium 7-chloro-2,1,3-benzoxadiazole-4-sulfonate | 81377-14-2 | 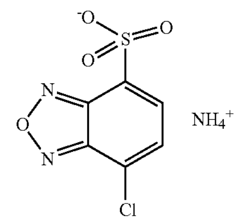 | C6H2ClN2O4S•H4N | 251.64434 (233.60588) |
| MO00766CB MO00766DA MO00766DE | 250 MG 1 GR 5 GR | 65.00 USD 142.00 USD 403.00 USD | 6-chloro-imidazo[2,1-b]thiazole-5-sulfonic acid amide | 112582-89-5 | 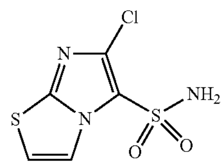 [SMILES: NS(=O)(=O)c1c(Cl)nc2sccn12] | C5H4ClN3O2S2 | 237.67866 |
| BTB06262DA BTB06262EA BTB06262EB | 1 GR 10 GR 25 GR | 23.00 USD 65.00 USD 115.00 USD | 8-chloro-naphthalene-1-sulfonic acid | 145-74-4 | 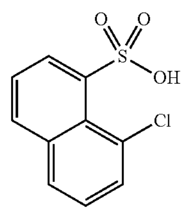 [SMILES: O=S(=O)(O)c1cccc2cccc(Cl)c12] | C10H7ClO3S | 242.67678 |
| BTB09138DA | 1 GR | 55.00 USD | 2-{[amino(imino)methyl]amino}-ethane-1-sulfonic acid | 543-18-0 | 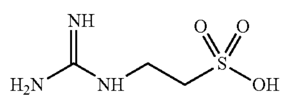 | C3H9N3O3S | 167.18276 |
| BTB13613DA BTB13613EA | 1 GR 10 GR | 53.00 USD 321.00 USD | 2-(4-amino-phenyl)-6-methyl-1,3-benzothiazole-7-sulfonic acid | 130-17-6 | 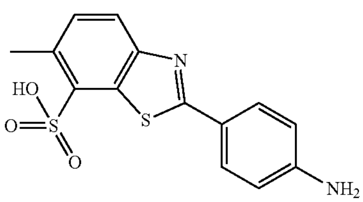 [SMILES: Cc1ccc2nc(-c3ccc(N)cc3)sc2c1S(=O)(=O)O] | C14H12N2O3S2 | 320.38088 |
| RJC04098DA RJC04098EA | 1 GR 10 GR | 53.00 USD 321.00 USD | 2,5-dibromo-4-(5-hydroxy-3-methyl-1H-pyrazol-1-yl)benzene-sulfonic acid dihydrate | 306935-68-2 | 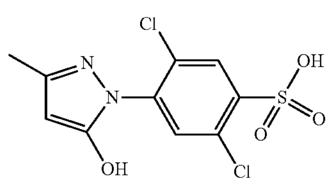 [SMILES: Cc1cc(O)n(-c2cc(Cl)c(S(=O)(=O)O)cc2Cl)n1] | C10H8Cl2N2O4S•2H2O | 359.18108 (323.15052) |
| SB01747DA SB01747EA SB01747EB | 1 GR 10 GR 25 GR | 42.00 USD 65.00 USD 115.00 USD | 3-amino-4-hydroxy-5-nitobenzene-1-sulfonic acid hydrate | 175278-60-1 | 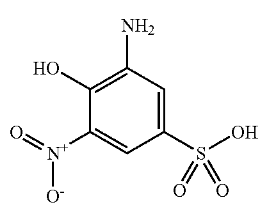 [SMILES: Nc1cc(S(=O)(=O)O)cc([N+](=O)[O-])c1O] | C6H6N2O6S•H2O | 252.19872 (234.18344) |

Table 9 recites non-limiting, representative, examples of sulfates suitable to be utilized as calcium sequestration or binding agents.

TABLE 9

| Product Code & Pack Size | | | Product Name | CAS | Structure | MF | MW |
|---|---|---|---|---|---|---|---|
| AC10430DA | 1 GR | 25.00 USD | 3-amino-phenylboronic acid 0.5 sulfate | 66472-86-4 | (3-aminophenylboronic acid hemisulfate structure) | C6H8 BNO2•0.5H2O4 S | 185.98176 (136.94502) |
| AC10430EA | 10 GR | 189.00 USD | | | | | |
| AC33706CB | 250 MG | 27.00 USD | Potassium 1H-indol-3-yl-sulfate | 2642-37-7 | (potassium indoxyl sulfate structure) | C8H6NO4S•K | 251.29824 (212.19994) |

Table 10 recites non-limiting, representative, examples of carboxylic acids suitable to be utilized as calcium sequestration or binding agents.

TABLE 10

Sigma-Aldrich
SAR COOH

| Brand | Catalog Number | MW |
|---|---|---|
| ALDRICH | 239569 | 86.09 |
| ALDRICH | 240168 | 88.11 |
| ALDRICH | D138606 | 100.12 |
| ALDRICH | 277827 | 116.16 |

TABLE 11

Sigma-Aldrich
SAR COOH

| Brand | Catalog Number | MW |
|---|---|---|
| ALDRICH | 242381 | 122.12 |
| ALDRICH | 117508 | 123.11 |
| ALDRICH | N7850 | 123.11 |
| ALDRICH | P42800 | 123.11 |

Table 11 recites non-limiting, representative, examples of aryl carboxylic acids suitable to be utilized as calcium sequestration or binding agents.

TABLE 11-continued

| | Sigma-Aldrich SAR COOH | |
|---|---|---|
| Brand | Catalog Number | MW |
| ALDRICH | P56100 | 124.10 |
| ALDRICH | P16621 | 138.15 |
| ALDRICH | T36404 | 136.15 |
| ALDRICH | 412244 | 140.12 |
| ALDRICH | 418846 | 140.12 |
| ALDRICH | 133750 | 148.16 |
| ALDRICH | B13055 | 150.14 |

TABLE 11-continued

| | Sigma-Aldrich SAR COOH | |
|---|---|---|
| Brand | Catalog Number | MW |
| ALDRICH | 135232 | 150.18 |

Table 12 recites non-limiting, representative, examples of cycloalkyl carboxylic acids suitable to be utilized as calcium sequestration or binding agents.

TABLE 12

| | Sigma-Aldrich SAR COOH | |
|---|---|---|
| Brand | Catalog Number | MW |
| ALDRICH | C116602 | 86.09 |
| ALDRICH | P20505 | 112.00 |
| ALDRICH | C112003 | 114.15 |
| ALDRICH | 339954 | 116.12 |
| ALDRICH | 341617 | 118.12 |
| ALDRICH | T32603 | 128.15 |

TABLE 12-continued

| Sigma-Aldrich SAR COOH | | |
|---|---|---|
| Brand | Catalog Number | MW |
| ALDRICH | 101834 | 128.17 |
| ALDRICH | 292915 | 129.12 |
| ALDRICH | 211872 | 129.18 |
| ALDRICH | 118008 | 129.16 |
| ALDRICH | P45850 | 129.18 |
| ALDRICH | 330604 | 142.20 |

TABLE 13

| Sigma-Aldrich SAR COOH | | |
|---|---|---|
| Brand | Catalog Number | MW |
| ALDRICH | 576301 | 188.18 |
| ALDRICH | 633739 | 188.19 |
| ALDRICH | 633832 | 139.17 |
| ALDRICH | B34702 | 198.22 |
| ALDRICH | B34729 | 198.22 |
| ALDRICH | 196487 | 212.25 |

Table 13 recites non-limiting, representative, examples of heteroaryl and biaryl acids suitable to be utilized as calcium sequestration or binding agents.

TABLE 13-continued

Sigma-Aldrich
SAR COOH

| Brand | Catalog Number | MW |
|---|---|---|
| ALDRICH | 197558 | 218.21 |
| ALDRICH | 590827 | 228.25 |

Table 14 recites non-limiting, representative, examples of ureas suitable to be utilized as calcium sequestration or binding agents.

TABLE 14

| Structure | Name |
|---|---|
| NH₂—C(=O)—NH₂ | Urea |
| H₂N—C(=O)—N(OH)H | Hydroxyurea |
| H₂N—C(=O)—NHNH₂ · HCl | Semicarbazide hydrochloride |
| H₂N—C(=O)—NHCH₃ | N-Methylurea |
| H₃CO—C(=NH)—NH₂ · H₂SO₄ | o-Methylisourea bisulfate |

Table 15 recites non-limiting, representative, examples of hydrazones suitable to be utilized as calcium sequestration or binding agents.

TABLE 15

| Structure | Name |
|---|---|
| Glyoxal mon-dimethylhydrazone structure | Glyoxal mon-dimethyl-hydrazone |
| Benzaldehyde semicarbazone structure | Benzaldehyde semicarbazone |
| Benzaldehyde p-nitrophenylhydrazone structure | Benzaldehyde p-nitrophenyl-hydrazone |
| 2-Hydroxybenzaldehyde phenylhydrazone structure | 2-Hydroxy-benzaldehyde phenyl-hydrazone |
| 2'-Aminoacetophenone phenylhydrazone structure | 2'-Amino-acetophenone phenyl-hydrazone |
| Valerophenone tosylhydrazone structure | Valero-phenone tosyl-hydrazone |

The "calcium sequestration agent" or "calcium binding agent" of the present invention is any agent capable of binding or sequestering calcium ion ($Ca^{II}$) such that the bound or sequestered calcium ion is prevented or inhibited (i.e., reduced) from interacting with other binding agents. In the context of the present invention, the calcium sequestration or binding agent, when administered to the skin of a patient in need of such treatment, binds or sequesters calcium ion in the local area of topical administration and regulates or modulates (i.e., prevents, limits, or inhibits) calcium from acting as a regulator in several (i.e., at least two) steps of melanogenesis and skin pigmentation.

The present composition contain a calcium sequestration or binding agent in an amount effective to reduce pigmentation. For example, the calcium sequestration or binding agent is present in the composition in an amount from about 0.1% to the solubility limit of the calcium sequestration or binding agent in the composition. Preferably, the calcium sequestration or binding agent is present in the composition in the amount of about 0.1% to about 25%, more preferably about 0.2% to about 10%, most preferably about 1% to about 5% by weight.

The pH range of any of the compositions containing a calcium sequestration or binding agent described herein is about 2.5 to about 9.0, preferably about 3.0 to about 7.0, more preferably about 4.0 to about 5.0. Solutions for adjusting pH to appropriate value, e.g., sodium hydroxide (NaOH), may be added to the composition of the present invention, as required.

Preferably, the agent capable of binding or sequestering calcium ion is a phosphate agent. A phosphate is defined as a form of phosphoric acid. The phosphate can contain one or more of phosphorus (P) atoms as follows:

i) one phosphorus atom (i.e., orthophosphates) such as $H_3PO_4$, any possible salts of $H_3PO_4$, or esters of $H_3PO_4$ as shown in FIG. 1 ii) two phosphorus atoms (i.e., pyrophosphates) such as $H_4P_2O_7$, any possible salts of $H_4P_2O_7$, or esters of $H_4P_2O_7$ iii) three phosphorus atoms (i.e., tripolyphosphates) such $H_5P_3O_{10}$, any possible salts of $H_5P_3O_{10}$, or esters of $H_5P_3O_{10}$ iv) more than three phosphorus atoms (i.e., polyphosphates) such as $H_{(n+4)}(PO_3)_{(n+2)}$, any possible salts of $H_{(n+4)}(PO_3)_{(n+2)}$, or esters of $H_{(n+4)}(PO_3)_{(n+2)}$ The structural formula of orthophosphate esters is shown in Formula I, where R1, R2 and R3 are each chosen from branched or unbranched alkyl or alkenyl groups having one or more carbon atoms.

Formula 1

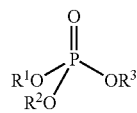

As used herein, the terms "phosphate" or "phosphates" does not include phosphate derivatives of ascorbic acid, such as sodium or magnesium ascorbyl phosphate, aminopropyl ascorbyl phosphate and other known phosphate derivatives of ascorbic acid with antioxidant properties.

Preferably, the composition can be prepared contains a phosphate form substantially free of calciums such as the phosphoric acid glycerophosphoric acid ($C_3H_9O_6P$). Glycerophosphoric acid can be present in two different chemical structures, including:

i) alpha-glycerophosphoric acid (also known as 3-glycerophosphate, 1-glycerophosphate, 3-phosphoglycerol, alpha-phosphoglycerol, glycerol-3-phosphate, glycerol 1-phosphate, glycerol-3-P, glycerophosphoric acid, 1-glycerophosphoric acid, alpha-glycerophosphate), and ii) beta-glycerophosphoric acid (also known as glycerol 2-phosphate, beta-glycerol phosphate, beta-GP, 2-glycerophosphoric acid, glycerophosphoric acid II).

More preferably, the compositions of the present invention contain the sodium salts of glycerophosphoric acid. The term "glycerophosphoric acid" includes alpha-glycerophosphoric acid, beta-glycerophosphoric acid, or any mixture thereof. Sodium salts of glycerophosphoric can further include the monosodium sodium salt of glycerophosphoric acid ($C_3H_8NaO_6P$), the disodium sodium salt of glycerophosphoric acid ($C_3H_7Na_2O_6P$), and/or any mixture of the mono- and disodium salts. Sodium salts of glycerophosphoric acid are herein referred as "sodium glycerophosphate".

The sodium glycerophosphate may further contain some bound water and may be in its hydrated form. The bound water is present in an amount of about 20 to about 40%; preferably between about 25 to about 35% per weight. For the present invention, the sodium glycerophosphate in accordance to the descriptions provided in European Pharmacopoeia $6^{th}$ Ed. (2007) represents one of the preferred forms and qualities of sodium glycerophosphate.

Excluding any calcium salts of glycerophosphoric acid, the composition may be prepared with other possible salts of glycerophosphoric acid such as the potassium salts of glycerophosphoric acid, the magnesium salts of glycerophosphoric acid, the manganese salts of glycerophosphoric acid, and/or any possible combination thereof including the sodium salts of glycerophosphoric acid. Those skilled in the art will recognize that calcium glycerophosphate or any other calcium salts of phosphoric acid are not phosphates free of calcium and, therefore, are not used in the present invention.

The compositions of the invention contain phosphate(s) in an amount effective to reduce pigmentation. For example, phosphate is present in the composition in an amount from about 0.1% to the solubility limit of the phosphate in the composition. Preferably, the phosphate is present in the composition in the amount of about 0.1% to about 25%, more preferably about 0.2% to about 10%, most preferably about 1% to about 5% by weight.

Preferably, the composition is prepared with sodium glycerophosphate ($C_3H_7Na_2O_6P\times H_2O$ according to specifications provided in European Pharmacopoeia $6^{th}$ Ed. (2007)) between about 1% to about 5% by weight.

The present invention also provides a skin lightening composition, which is well tolerated. Preferably, such skin lightening compositions provide less skin irritation than is commonly observed with several of the skin lightening products containing hydroquinone; in particular those skin lightening products with additionally contain chemicals with known human skin irritant properties such as retinoic acid, tretinoin, retinol, alpha hydroxy acids such as glycolic or lactic acid, beta hydroxyl acids such as salicylic acid, azelaic acid, free short chain fatty acids, free short chain fatty acid esters, ionic surfactants such as SLS or SLES. Examples of skin lightening products containing hydroquinone along with chemicals with known human skin irritant properties, include, but are not limited to, Tri-Luma® (from Galderma), EpiQuin® Micro (from SkinMedica), Obagi Nu-Derm® Clear and Obagi Nu-Derm® Blender (both from OMP, Inc.) and Lustra® Hydroquinone USP 4% (from TaroPharma).

Specifically, the compositions of the present invention are well tolerated and do not (or only minimally) lead to visibly noticeable skin redness (i.e., erythema, contact dermatitis) or rash (i.e., edema, contact allergy, uticaria) when used once to twice daily for a prolonged period of time (i.e., more than two weeks) under normal in use conditions typical of a skincare or dermatological product. More specifically, the compositions of the present invention provide less skin irritation as compared to skin lightening products containing hydroquinone as observed in repetitive skin irritancy patch tests in humans or animals realized according to the art-recognized models described in J. Toxicol.-Ot. & Ocular Toxicol., 1 (2); 109-115. 1982; Contact Dermatitis, 20(1); 3-9. 1989; Lanman, B. M., E. B. Elvers, and C. J. Howard, 1968, "The Role of Human Patch Testing in a Product Development Program," Joint Conference on Cosmetic Sciences, The Toilet Goods Association (currently, the Cosmetic, Toiletry and Fragrance Association), Washington, D.C., Apr. 21-23, 1968 and Patel, S. M., E. Patrick, and H. I. Maibach, 1976, "Animal, Human, and In Vitro Test Methods for Predicting Skin Irritation," Dermatotoxicology, Chpt. 33, 5th Ed., Eds. F. N. Marzulli, H. I. Maibach, Taylor, and Frances) (each of which are incorporated herein by reference).

Preferably, the present invention provides methods and compositions for skin depigmentation which are effective in concentrations not resulting in significant skin irritancy as determined by the art-recognized models described herein. Preferably, the present invention provides compositions which are substantially free of calcium, steroids, parabens, anti-microbial preservatives and/or formaldehyde releasers The term "substantially free" as used herein means that the composition of interest (e.g., calcium) is present in the composition in an amount less than 0.1% per weight, preferably less than 0.5% by weight and most preferably less than 0.01% per weight. Preferably, the present invention provides compositions which are suitable for topical application, cosmetically elegant and fast absorbing. That is, the compositions of the present invention do not provide sticky, oily, greasy or otherwise unpleasant feeling when applied onto skin after about one to maximum of about two minutes of application; in case applied as dose per skin area typical for skincare or dermatological products (typically less than 1 mg of composition per $cm^2$).

Additional Active Agents

The present invention also provides stable skin lightening composition, which contain at least one calcium sequestration or binding agent, as described above, and which may further contain at least one additional active agent capable or modulating or reducing (as assessed in vitro and/or in vivo) at least one of the following steps in melanogenesis:

i) uptake of L-tyrosine into melanocytes, and/or
ii) uptake of L-phenylalanine into melanocytes, and/or
iii) turnover of phenylalanine into tyrosine by phenylalanine hydroxylase, and/or
iv) uptake of L-tyrosine into melanosomes, and/or
v) turnover of L-tyrosine into L-Dopa by tyrosinase or tyrosine hydroxylase, and/or
vi) turnover of L-Dopa into dopaquinone by tyrosinase, and/or
vii) transfer of melanosome from melanocytes to keratinocytes.

Several compounds can be described as compounds capable of competing with the transport (active uptake into cell or cell organelle) of L-tyrosine into melanocytes and/or into melanosomes, what may result in a reducing or limiting pool of L-tyrosine for melanogenesis.

Amino Acids

Several amino acids are known competitively inhibit the uptake of L-tyrosine into melanocytes and/or melanosomes. Amino acids L-alanine, glycine, L-isoleucine, L-leucine, but not their D-forms, were described to have hypopigmenting effects in an in vitro assay using B16F0 melanoma cells as cell model for studying melanogenesis. (See Biol Pharm Bull 30, 2007, pp. 677-681). These amino acids were shown not to function as inhibitors of tyrosinase.

Another compound potentially inhibiting tyrosine transport is the sulfur homologue of tyrosine 4-S-cysteinylphenol. (See Biochem J 280, 1991, pp. 721-725). 4-S-cysteinylphenol may also act as substrate of tyrosinase and can therefore be also regarded as inhibitor of tyrosinase. There is some evidence that amino acids L-phenylalanine and L-tryptophan also compete for tyrosine transport. (See Biochem J 280, 1991, pp. 721-725; J Biol Chem 271, 1996, pp. 4002-4008). However, phenylalanine is a precursor of melanin and is therefore excluded in the present invention. L-Tyrosine is formed from L-phenylalanine in the presence of enzyme phenylalanine hydroxylase in melanocytes. Similarly, tryptophan is excluded in the present invention.

Thus, the compositions of the present invention can contain at least one calcium sequestration or binding agent and can further contain L-alanine, glycine, L-isoleucine, L-leucine or a combination thereof. L-alanine, glycine, L-isoleucine, L-leucine can also include esters (e.g. R—COOR' with R=from amino acid and R'=branched or not branched alky/aryl side chain consisting of up to 18 carbons), amides (R—NH(C=O)— R'), with R=from amino acid and R'=branched or not branched alky/aryl side chain consisting of up to 18 carbons) or both to increase their skin bioavailability. These amino acids also include zwitterions with a sodium or potassium as positive ion (cation).

The present composition can also contain amino acids or their respective derivatives (esters, amides, etc.) in an amount effective to reduce pigmentation or reduce the transport of L-tyrosine either into the melanocyte and/or into the melanosome. For example, the amino acid is present in the composition in an amount from about 0.001% to the solubility limit of the amino acid in the composition. Preferably, the amino acid is present in the composition in the amount of about 0.01% to about 10%, more preferably about 0.05% to about 5%, most preferably about 0.1% to about 2% by weight.

In one embodiment, the invention provides a composition containing one or more phosphates, substantially free of calcium, and further containing L-leucine in an amount of about 0.1% to about 2% by weight. Preferably, the present invention provides a composition containing sodium glycerophosphate ($C_3H_7Na_2O_6P \times H_2O$; according to specifications provided in Ph. Eur. $6^{th}$ Ed.) in an amount of about 1% to 5% by weight and further contains L-leucine in an amount of about 0.1% to 2% by weight.

Tyrosinase Inhibitors

The compositions of the present invention can contain at least one calcium sequestration or binding agent and may further contain one or more compounds capable of reducing (as assessed in vitro and/or in vivo) the turnover of L-tyrosine into L-Dopa by tyrosinase or tyrosine hydroxylase, and/or the turnover of L-Dopa into dopaquinone by tyrosinase. Compounds which reduce the turnover of L-tyrosine into L-Dopa and/or reduce the turnover of L-Dopa into dopaquinone are generally referred as tyrosinase inhibitors meaning that they inhibit of tyrosinase activity, tyrosinase gene expression, and/or tyrosine protein formation and/or maturation.

For example, the following compounds have been described to act as tyrosinase inhibitors as assessed in diverse in vitro enzymatic and cellular assays (see Journal of Medicinal Chemistry 42 (2007) 1370-1381 [including supporting information mentioned under Appendix A]; Pigment Cell Res 19, 2006, pp. 550-571) (incorporated herein by reference) and are therefore suitable to be incorporated, either alone or in combination, into the compositions described herein: hydroquinone (1,4-benzenediol); diphenylmethane derivatives (see WO 2004/105736; incorporated herein by reference) including but not limited to 4-(1-phenylethyl)1,3-benzenediol (phenylethyl resorcinol); kojic acid; alpha-arbutin; beta-arbutin; deoxyarbutin, L-mimosine; monobenzyl ether of hydroquinone; hydroquinone fatty esters; L-tropolone; ascorbic acid; benzoic acid; oxyresveratrol (i.e., 2,4,3',5'-tetrahydroxystilbene); quercetin; benzaldehyde; aloesin; trans-resveratrol; anisaldehyde; cinnamic acid; gnetol; dihydrognetol; 3,3',4-hydroxy-trans-stilbene; 3,3',4,4'-hydroxy-trans-stilbene; 3-amino-L-tyrosine, 2-aminophenol; isoliquiritigenin; 4-hydroxychalcone; butein; 4'-hydroxychalcone; 2',4'-dihydroxychalcone; 2',4-dihydroxychalcone; trans-4-azobenzene carboxylic acid; cis-4-azobenzene carboxylic acid; trans-4, 4'-azobenzene dicarboxylic acid; cis-4,4'-azobenzene dicarboxylic acid; castanospermine; deosynojirimycin; Ko-YGC; Ko-YGV; Ko-YGE; Ko-YGT; Ko-YGL; Ko-YGW; Ko-YGF; Ko-YGH; Ko-YGN; Ko-YGD; Ko-YGG; Ko-YIG; Ko-YYG; Ko-YSG; Ko-YMG; Ko-YQG; Ko-YRG; Ko-YHG; Ko-YNG; Ko-YDG; Ko-FIY; Ko-FRY; Ko-FYY; Ko-FWY; Ko-FFY; Ko-KWY; Ko-KRY; Ko-KKY; Ko-KIY;

Ko-FWW; Ko-FWF; Ko-FWI; Ko-FWD; Ko-WWY; glabridin; N-cyclopenthyl-N-nitrosohydroxyl-amine; N-benzyl-N-nitrosohydroxylamine; N-benzyl-N-nitrosohydroxylamine; N-cyclopenthyl-N-nitrosohydroxyl-amine; 3,5-dihydroxy-4'-methoxystilbene; 3,4'-dimethoxy-5-hydroxystilbene; piceid; rhapontigenin; rhaponticin; kurarinone; kushnol F; 4-hydroxyanisol; 2-hydroxy-4-methoxy benzaldehyde; cuminaldehyde; artocarbene; norartocarpanone; 4-propylresorcinol; 3,4-dihydroxybenzonitrile; 3,4,2,4-trans-stilbene; artogomezianol; andalasin; crocusatins H; crocin-1; crocin-3; 3,4-dihydroxycinnamic acid; 4-hydroxy-3-methoxycinnamic acid; anisic acid; 2-methoxycinnamic acid; 3-methoxycinnamic acid; 4-methoxycinnamic acid; kaempferol; glabrene; pyridoxine; Pyridoxamine; Pyridoxal; Pyridoxamine 5'-phosphate; Protocatechuic acid methyl ester; Protocatechuic acid; m-coumaric acid; 3-caffeoylquinic acid; 4-caffeoylquinic acid; 5-caffeoylquinic acid; 3,4-dicaffeoylquinic acid; Caffeic acid; Fisetin; 3,7,4'-trihydroxyflavone; Morin; Luteolin; Apigenin; Galangin; Diethyldithiocarbamate; Phenylthiourea; Phloroglucinol; Eckstolonol; Eckol; Phlorofucofuroeckol; Dieckol; HPABS; Gluthatione; B-Mercaptoethanol; Protocatechualdehyde; 8'-epi-cleomiscosin A; 3,4-Dihydroxybenzaldoxime; 3-Hydroxy-4-methoxybenzaldoxime; 3,4,5-Trihydroxybenzaldoxime; 4-Hydroxy-3-methoxy benzaldoxime; 3-Ethoxy-4-hydroxy benzaldoxime; 4-Hydroxybenzaldoxime; 3,4-Dihydroxybenzaldehyde-O-ethyloxime; 3,4-Dihydroxybenzaldehyde-O-(4-methylbenzyl)-oxime; 3-Hydroxy-4-methoxy benzaldehyde-O-ethyloxime; 3,4,5-Trihydroxybenzaldehyde-O-ethyloxime; 4-Hydroxy-3-methoxybenzaldehyde-O-ethyloxime; 3-Ethoxy-4-hydroxybenzaldehyde-O-ethyloxime; 4-Hydroxybenzaldehyde-O— ethyloxime; 4-Hydroxy-3-methylbenzaldehyde-O-ethyloxime; 3,5-Dimethyl-4-hydroxybenzaldehyde-O-ethyloxime; (+)-Androst-4-ene-3,17-dione; Androsta-1,4-diene-3,17-dione; 17β-Hydroxyandrosta-1,4-dien-3-one; 11α-Hydroxyandrost-4-ene-3,17-dione; 17β, 11α-Dihydroxyandrost-4-en-3-one; Esculetin; Lappaconitine; Stigmast-5-ene-3β,26-diol; Stigmast-5-ene-3β-ol; Campesterol; *arctostaphylos uva ursi* (bearberry) leaf extract; *glycyrrhiza glabra* (licorice) extract; *sanguisorba officinalis* (burnet) extract; *scutellaria baicalensis* root (skull cap) extract; and *morus alba* (mulberry) extract; pinosylvin, dihydropinosylvin; gallic acid; gentisic acid; methyl gentisate; epigallocatechin-3-O-gallate; epigallocatechin; green tea leave extract; ellagic acid; pyognol; *myrica rubra* leave extract; and/or octadecenedioic acid.

In addition to these recited tyrosinase inhibitors, any biological precursors (pro-forms) of above chemicals can also be included in the present invention. Biological precursors can be simple esters (i.e. methyl-, ethyl-, propyl-, or butyl-esters) of inhibitors with carboxy group. Also included are derivatives of ascorbic acid, such as aminopropyl ascorbyl phosphate, magnesium ascorbyl phosphate, alkyl esters of L-ascorbic acid such as L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; as well as their sodium, potassium, magnesium and/or manganese salts.

The present composition may contain at least one tyrosinase inhibitor in an amount effective to reduce pigmentation or reduce the turnover of L-tyrosine into L-Dopa by tyrosinase or tyrosine hydroxylase, and/or the turnover of L-Dopa into dopaquinone by tyrosinase. For example, the tyrosinase inhibitor can be present in the composition in an amount from about 0.001% to the solubility limit of the tyrosinase inhibitor in the composition. Preferably, the tyrosinase inhibitor is present in the composition in the amount of about 0.01% to about 15%, more preferably about 0.05% to about 10%, most preferably about 0.1% to about 5% by weight.

The present invention provides a composition containing one or more phosphates, substantially free of calcium, and further containing: a) hydroquinone (1,4-benzenediol) in an amount of about 0.1% to about 10% by weight, b) 4-(1-phenylethyl)1,3-benzenediol (phenylethyl resorcinol) in an amount of about 0.1% to about 5% by weight, c) arbutin in an amount of about 0.1% to about 10% by weight, d) bearberry leaf extract in an amount of about 0.1% to about 10% by weight, e) kojic acid in an amount of about 0.1% to about 5% by weight, f) oxyresveratrol in an amount of about 0.1% to about 5% by weight, and/or g) gnetol in an amount of about 0.1% to about 5% by weight.

The compositions of the invention may contain, in some embodiments, one or more phosphates, substantially free of calcium, and may further contain hydroquinone (1,4-benzenediol) in an amount of about 1% to about 10% by weight and/or may further contain 4-(1-phenylethyl)1,3-benzenediol (phenylethyl resorcinol) in an amount of about 0.1% to about 5% by weight Melanosome Transfer Inhibitors In some embodiments, the compositions of the present invention contain at least one calcium sequestration or binding agent and may additionally contain one or more compounds capable of reducing (as assessed in vitro and/or in vivo) the transfer of melanosomes from melanocytes to keratinocytes. Inhibitors of the transfer of melanosomes from melanocytes to keratinocytes have been described previously (see Pigment Cell Res 19, 2006, pp. 550-571) and include, for example, niacinamide (vitamin B3); centaureidine; lectins; neoglycoproteins and certain inhibitors of serine proteases. In addition, N-acetyl-glucosamine may also reduce melanosome transfer.

The present composition may contain at least one melanosome transfer inhibitor in an amount effective to reduce pigmentation or reduce the transfer of melanosomes from melanocytes to keratinocytes. For example, the melanosome transfer inhibitor can be present in the composition in an amount from about 0.001% to the solubility limit of the melanosome transfer inhibitor in the composition. Preferably, the melanosome transfer inhibitor is present in the composition in the amount of about 0.01% to about 12%, more preferably about 0.05% to about 6%, most preferably about 0.1% to about 3% by weight.

The invention provides a composition containing one or more phosphates, substantially free of calcium, and may further contain hydroquinone in an amount of about 0.1% to about 10% by weight, and further containing a melanosome transfer inhibitor in an amount of about 0.1% to about 3% by weight.

For example, the present invention also provides a composition including one or more phosphates, substantially free of calcium, and also includes 4-(1-phenylethyl)1,3-benzenediol (phenylethyl resorcinol) in an amount of about 0.1% to about 5% by weight, and may also include a melanosome transfer inhibitor in an amount of about 0.1% to about 3% by weight.

In one embodiments, the invention additionally provides a composition containing one or more phosphates, substantially free of calcium; hydroquinone in an amount of about 0.1% to about 10% by weight; 4-(1-phenylethyl)1,3-benzenediol (phenylethyl resorcinol) in an amount of about 0.1% to about 5% by weight: and a melanosome transfer inhibitor in an amount of about 0.1% to about 3% by weight.

Melanocortin Receptor 1 Inhibitors

The compositions of the present invention can contain at least one calcium sequestration or binding agent and can further contain one or more compounds capable of decreasing (as assessed in vitro and/or in vivo) melanocortin receptor 1 (MC1R) activity. For instance, agouti signaling protein regulates skin pigmentation by antagonizing the binding of α-MSH to MC1R. (See Abdel-Malek et al., J. Cell Sci. 2001, 114 (Pt.5):1019-24; Jordan and Jackson, Bioessays. 1998, 20(8):603-606; Voisey and Van Daal, Pigment Cell Res. 2002; 15(1):10-18; Wolff, Pigment Cell Res. 2003, 16(1):2-15). The signaling inhibition through the receptor results from two effects (i) a direct competition at the binding site, and (ii) a downregulation of the receptor signaling. (See Barsh et al., Pigment Cell Res., 2000, 13 Suppl. 8:48-53). As an example, undecylenoyl phenylalanine was described to have an affinity towards MC1R and was shown to act as antagonist of α-MSH in vitro.

In some embodiments, the present composition contains at least one α-MSH antagonist in an amount effective to antagonizing the binding of α-MSH to MC1R. For example, the α-MSH antagonist is present in the composition in an amount from about 0.001% to the solubility limit of the α-MSH antagonist in the composition. Preferably, the α-MSH antagonist is present in the composition in the amount of about 0.01% to about 10%, more preferably about 0.05% to about 5%, most preferably about 0.1% to about 4% by weight.

In one embodiment, the present invention provides a composition containing one or more phosphates, substantially free of calcium, and also contains hydroquinone in an amount of about 0.1% to about 10% by weight and an α-MSH antagonist in an amount of about 0.1% to about 4% by weight. By way of non-limiting example, the α-MSH antagonist is undecylenoyl phenylalanine (with chemical structure: $CH_2=CH-(CH_2)_8-CO-NH-CH(-COOH)(-CH_2-C_6H_5)$, as described in WO2003/061768].

Preferably, the present invention additionally provides a composition containing one or more phosphates, substantially free of calcium; 4-(1-phenylethyl)1,3-benzenediol by weight in an amount of about 0.1% to about 5% by weight; and an α-MSH antagonist in an amount of about 0.1% to about 4% by weight. By way of non-limiting example, the α-MSH antagonist is undecylenoyl phenylalanine.

Alternatively, the present invention also provides a composition including one or more phosphates, substantially free of calcium; hydroquinone in an amount of about 0.1% to about 10% by weight; 4-(1-phenylethyl)1,3-benzenediol by weight in an amount of about 0.1% to about 5% by weight; and an α-MSH antagonist in an amount of about 0.1% to about 4% by weight. Preferably, the α-MSH antagonist is undecylenoyl phenylalanine.

Also provided are compositions containing one or more phosphates, substantially free of calcium; hydroquinone in an amount of about 0.1% to about 10% by weight; 4-(1-phenylethyl)1,3-benzenediol by weight in an amount of about 0.1% to about 5% by weight; and an α-MSH antagonist in an amount of about 0.1% to about 4% by weight. For example, the α-MSH antagonist is undecylenoyl phenylalanine. These compositions may additionally contain a melanosome transfer inhibitor in an amount of about 0.1% to about 3% by weight.

Dermatological Drugs, Biologics and Skin Care Additives

Any of the compositions of the present invention can include at least one calcium sequestration or binding agent and can further include one or more compounds, skincare actives or dermatology drugs and/or biologics other than calcium containing chemicals known in the arts of the treatment of skin pigmentation; general dermatology; cosmetic dermatology; skincare such as, for example skin moisturization; or rejuvenation, including but not limiting to, transforming growth factor (including TGF-beta1, TGF-beta2, TGF-beta3); collagen stimulators such as certain growth factors (e.g. PDGFs, FGFs, etc.) and/or certain peptides (e.g., Matrixyl-3000); stimulators of keratinocyte proliferation such as (e.g. EGF, KGFs, etc.); inhibitors of collagen degrading enzymes (e.g., natural or synthetic inhibitors of MMPs); inhibitors of elastin degrading enzymes (e.g., natural or synthetic inhibitors of elastase); appropriate antioxidants (such as vitamin C, vitamin E, ferulic acid, lipoic acid, polyphenols, ergothioneine, etc.) and their derivatives; appropriate sunscreens and/or solar UV reflectors (e.g., spheres and/or microparticles made of polymers, etc.); anti-inflammatory agents (e.g., steroids, non-steroidal anti-inflammatory agents, anti-inflammatory interleukins, IL-Ira, etc.); emollients; humectants (e.g., glycerin, urea, hyaluronic acid, natural moisturizing factors, etc.); inhibitors of neurotransmitter release; skin penetration agents (e.g., oleic acid, propylene glycol, etc.); skin protectants (e.g., allantoin, calamine, coca butter, cod liver oil, colloidal oatmeal, dimethicone, glycerin, hard fat, kaolin, lanolin, mineral oil, petrolatum, topical starch, white petrolatum, etc.); vitamins (e.g., vitamin B3, vitamin B5, vitamin B6, vitamin D, vitamin F, etc.) and derivatives thereof; keratolytic agents (e.g., urea, alpha-hydroxyl acids (e.g., lactic acid, glycolic acid, citric acid, etc.), beta-hydroxyl acids (e.g., salicylic acid, etc.), and polyhydroxyacids, etc.)); external analgesic agents (e.g., benzocaine, butamben picrate, dibuccaine, diemethisoquin, dyclonine, lidocaine, pramoxine, tetracaine, etc.) and their respective salts; antipruritic agents; cell metabolism stimulants (e.g., pantothenic acid, niacin, nicotinic acid esters, etc.); appropriate anti-acne agents; astringents; counter irritants; antihistamine agents; azelaic acid; retinoic acid, retinol and/or derivatives; natural oils (e.g., jojoba oil, shea butter, etc.); appropriate biological components (e.g., cell lysate, human dermal fibroblast lysate, conditioned cell culture medium, stem cell components, etc.); mixtures of growth factors (e.g., PSP® from Neocutis Inc, Nouricel-MD® from SkinMedica Inc., etc.); and/or wound healing agents.

Formulations and Modes of Administration

Those skilled in the art will recognize that any of the compositions of the present invention can contain at least one calcium sequestration or binding agent and can further contain one or more compounds capable of chemically stabilizing any of the ingredients present in the composition. Compounds that help to chemically stabilize any of the ingredients may include, but are not limited to, sodium metabisulfite; sodium bisulfate; BHT; BHA; propyl gallate; disodium EDTA; lemon extract; antioxidants, including ascorbic acid (vitamin C) and its derivatives such as phosphate derivatives of ascorbic acid including sodium or magnesium ascorbyl phosphate, aminopropyl ascorbyl phosphate, and other known phosphate derivatives of ascorbic acid having antioxidant properties; and tocopherol and derivatives of tocopherol such as, sodium vitamin E phosphate (VEP), lauryl imino dipropionic acid tocopheryl phosphate, tocopheryl glucoside, tocopheryl succinate, tocophersolan (tocopheryl polyethylene glycol 1000 succinate), disodium lauriminodipropionate tocopheryl phosphates, tocophereth-5, 10, 12, 18, and 50 (polyethylene glycol (PEG) tocopheryl ethers. Sulfites such as sodium metabisulfite, and/or sodium bisulfate are particularly useful to stabilize hydroquinone or other chemically labile (i.e., easily being oxidized) compounds present in the said composition. In general, the compositions may contain between about 0.05 to 0.5% sulfites by weight.

The compounds, compositions and formulations of the instant invention can be administered by any means known in the art. Preferably, the compositions of the present invention are formulated as a topical preparation or dosage form. Topical preparations are ointments, creams, gels and lotions. The definition of these topical dosage forms is given by Bhuse L. et al. (Int J Pharm 295: 2005, 101-112) (incorporated by reference). The carrier can also be a liquid, a foam, a mousse, a spray, an aerosol, an oil-in-water emulsion, a water-in-oil emulsion, a triple emulsion, a nanoemulsion, a microemulsion, a hydrogel, a solution, a paste, a jelly, a patch, a wipe, a cloth, and/or a dispersion or suspension. The carrier may contain niosomes, liposomes, nanospheres, microspheres, nanoparticles, microparticles, lipid droplets, solid particles, pigments and/or water droplets.

In one preferred embodiment, the carrier is a cream. In various embodiments, the cream may be either an oil-in-water mixture, or a water-in-oil based carrier. In another preferred embodiment, the carrier is a gel or hydrogel.

Those skilled in the art will recognize that any reference herein to a composition of the invention includes any composition containing one or more phosphates free of calcium in conjunction with a carrier.

Those skilled in the art will also recognize that additional agents can be added in any of the methods and compositions of the invention. These agents may include, but are not limited to, e.g., antimicrobial agents (e.g., parabens, phenoxyethanol, chlorophenesin, propylene glycol, butylene glycol, ethylhexylglycerin, imidazolidinyl urea, methylchloroisothiazolinone, potassium benzoate, DMDM hydantoin, etc.), etc.), color additives, fragrances, sensory stimulating agents, polymers, surfactants, water, oils, etc. Information regarding the preparation of compositions, can be found, e.g., in Volume 3: Liquid Products, Volume 4: Semisolid Products and Volume 5: Over-the-Counter Products, of the 'Handbook of Pharmaceutical Manufacturing Formulations' (edited by S. K. Niazi, CRC Press, Boca Raton, 2004). Moreover, information regarding the preparation of cosmetic or cosmeceutical compositions may be found in the formulary archive of the Happy Magazine (see http://www.happi.com/formulary). In addition, formulary information for cosmetic or cosmeceutical compositions can be also obtained from diverse ingredient suppliers such as Croda, Ciba, BASF, Dow Chemicals, etc.

The present invention provides stable and none to little irritating (i.e., no or only limited and acceptable skin irritancy) compositions for topical application to the skin to treat skin pigmentation disorders, such as melasma, post-inflammatory hyperpigmentation, pigmentation changes due to skin aging, or any other skin conditions related with normal such as skin of color or abnormal pigmentation such as hypo- or hyper-pigmentation in humans.

Stable compositions can be obtained by (1) selecting appropriate calcium sequestration or binding agent concentration(s), (2) selecting appropriate salt form(s) of the agent other than calcium salt(s), (3) adjusting the pH of the composition, (4) selecting appropriate type of formulation (e.g., liquid, a foam, a mousse, a spray, an aerosol, an oil-in-water emulsion, a water-in-oil emulsion, a triple emulsion, a nanoemulsion, a microemulsion, a hydrogel, a solution, a paste, a jelly, a patch, a wipe, a cloth, and/or a dispersion or suspension) for the composition, (5) selecting appropriate ingredients allowing to stabilize the composition, (6) selecting and appropriate container for composition suitable for topical administration (e.g., tube, airless pump, jar, vial, monodose, etc.), and/or (7) selecting conditions allowing the preparation of a stable preparation (e.g., preparation of composition under inert gas, etc.).

The term "stable" when applied to the compositions of the instant invention is defined as having a comparable color when the composition is placed on a flat and inert surface (i.e., removed from its container) under normal ambient air and light conditions (i.e., air and light conditions as normally exist in the living room at home) when kept for at least one month at room temperature (about 25° C.).

Other than the above-defined color stability, stability of the composition may further include physical stability (e.g., viscosity, odor, appearance, texture, etc.) and chemical stability of the selected active(s) such as a drug active (e.g., calcium sequestration agent, hydroquinone, etc.). Chemical stability can be assessed using HPLC or other appropriate analytical methods. When the composition is placed (e.g., filled) into a suitable container (e.g., a tube, pump, jar, etc.), the composition should be chemically stable (i.e., less than a ±10% change in the content as compared to the baseline value) for at least a year under normal storage condition (i.e., room temperature; or common temperature fluctuations occurring in house/living room/bath room due to changes in season or geographical region). Stability may also be tested under accelerated conditions at elevated temperatures (e.g., 40° C. or higher) in order to predict stability of the composition at room temperature (about 25° C.).

The compositions of the present invention may be applied to the entire body, including the face. These compositions may be applied as needed or alternatively, as part of a skin care routine. Preferably, the composition is applied weekly. More preferably, the composition is applied once daily at night at least half an hour before bedtime. However, it can be also applied twice daily, with the preferred mode being once in the morning and once in the evening. When compositions are applied twice daily, the compositions may be the same or different for each application. For example, the same composition may be applied twice daily or alternately, one composition may be applied in the morning and a second, different composition, may be applied in the evening. The compositions can be applied to any mammal (e.g., a primate, rodent, feline, canine, domestic livestock (such as cattle, sheep, goats, horses, and pigs). Preferably, the compositions are applied to humans.

In some embodiments, a sunscreen formulation offering a SPF 15 or higher is used in addition during day time in order to protect skin from sun exposure or damage. Additionally, the compositions of the present invention may further contain one or more sunscreen active agents, such as those that provide a UV-B filter and, in some embodiments, additionally a UV-A filter. Examples of suitable UV-A and UV-B filters include those described in U.S. Pat. No. 7,078,022 (incorporated herein by reference).

Preferably, the compositions of the invention dry quickly and cleanly (without visible residue or significant stickiness) after application of a normal amount (i.e., 0.2 to 2 mg composition per $cm^2$) on the skin.

The examples as set forth herein are meant to exemplify the various aspects of carrying out the invention and are not intended to limit the invention in any way. Unless otherwise specified, it is to be understood that the concentrations of the component ingredients in the compositions of the invention are in %, w/w, based on the total weight of the composition.

Example 1

Exemplary compositions formulated in accordance with the present invention are presented in Table 19. These compositions serve as illustrative formulations which provide several of the advantageous features of the invention, namely, mildness to the skin after application with no or only limited skin irritancy; clearness and non-greasiness upon application (transparent) to face and other skin areas other than the palms and the soles; and quick-drying, particularly when the compositions are preferably formulated as water-in-oil formulations.

TABLE 19

| NO. | PHASE | INGREDIENT (TRADE NAME) | INCI DESIGNATION | SUPPLIER | % BY WEIGHT |
|---|---|---|---|---|---|
| 1 | A | DEIONIZED WATER | WATER (AQUA) | | 63.310 |
| 2 | A | NA$_2$EDTA | DISODIUM EDTA | AKZO/DEWOLF | 0.100 |
| 3 | A | KELTROL CG-T | XANTHAN GUM | CP KELCO/UNIVAR | 0.300 |
| 4 | B | LIPOWAX D | CETEARYL ALCOHOL CETEARETH-20 | LIPO | 8.250 |
| 5 | B | LIPO GMS 450 | GLYCERYL STEARATE | LIPO | 6.000 |
| 6 | B | CERAPHYL 230 | DIISOPROPYL ADIPATE | ISP SUTTON | 5.000 |
| 7 | B | DC TORAY FZ-3196 | CAPRYLYL METHICONE | DOW CORNING/UNIVAR | 3.000 |
| 8 | B | DC 200 FLUID 100 CST | DIMETHICONE | DOW CORNING/UNIVAR | 1.000 |
| 9 | B | LIPOVOL J | *SIMMONDSIA CHINENSIS* (JOJOBA) SEED OIL | LIPO | 1.000 |
| 10 | B | SHEA BUTTER HMP | *BUTYROSPERMUM PARKII* (SHEA BUTTER) | EARTH SUPPLIED PRODUCTS | 1.000 |
| 11 | B | VITAMIN E ACETATE OIL (USP, FCC) | DL-ALPHA TOCOPHERYL ACETATE | BASF/CHEMCENTRAL | 0.200 |
| 12 | C | DEIONIZED WATER | WATER (AQUA) | | 0.100 |
| 13 | C | ELESTAB CPN ULTRA PURE | CHLORPHENESIN | COGNIS | 0.300 |
| 14 | C | PHENOXETOL | PHENOXYETHANOL | CLARIANT | 0.600 |
| 15 | C | SEPIWHITE MSH | UNDECYLENOYL PHENYLALANINE | SEPPIC | 0.500 |
| 16 | C | SODIUM GLYCEROPHOSPHATE (Ph. Eur. 6 Ed, Item# 500012045500) | SODIUM GLYCEROPHOSPHATE | DR. PAUL LOHMANN | 3.000 |
| 17 | C | L-LEUCINE | LEUCINE | AJINOMOTO | 1.000 |
| 18 | C1 | CITRIC ACID 50% SOLUTION (TO pH 4.5-5.0) | CITRIC ACID | PCI | 1.920 |
| 19 | C2 | GLYCERIN 99.7% (USP) | GLYCERIN | ACME-HARDESTY | 2.000 |
| 20 | C2 | SYMWHITE 377 | PHENYLETHYL RESORCINOL | KAH/SYMRISE | 0.500 |
| 21 | C2 | VITAGEN | AMINOPROPYL ASCORBYL PHOSPHATE | BASF | 0.500 |
| 22 | D | SIMULGEL INS 100 | HYDROXYETHYL ACRYLATE/SODIUM ACRYLOYLDIMETHYL TAURATE COPOLYMER ISOHEXADECANE POLYSORBATE 60 | SEPPIC | 0.420 |
| TOTAL | | | | | 100.00 |

Such compositions (e.g., Table 19) were generally prepared in a clean and sanitized stainless steel vessel, which was suitable for blending products containing hydroquinone, as described herein below:

PHASE A: DISPERSE KELTROL IN WATER, MIX UNTIL ALL HYDRATES;
  ADD REMAINING PHASE A INGREDIENTS, HEAT TO ABOUT 75° C. WHILE MIX UNTIL ALL DISSOLVES.
PHASE B: COMBINE PHASE B INGREDIENTS IN A SEPARATE VESSEL AND MIX WHILE HEATING TO 75° C.; ONCE ALL WAXES MELT AND PHASE IS AT TEMP AND UNIFORM, SLOWLY ADD TO PHASE A; COOL TO 35° C.
PHASE C: COMBINE PHASE C INGREDIENTS WITH MECHANICAL STIRRING UNIT AND MIX WITH MODERATE AGITATION
PHASE C1: USE PHASE C1 TO ADJUST pH OF PHASE C TO 4.0-4.5
PHASE C2: COMBINE PHASE C2 AND MIX WHILE HEATING SLIGHTLY TO 40° C.; CONTINUE MIXING UNTIL POWDERS DISSOLVE THEN ADD TO PHASE C; ADD PHASE C TO BATCH WITH MODERATE AGITATION
PHASE D: ADD PHASE D TO BATCH, MIX UNTIL UNIFORM; HOMOGENIZE THE BATCH AT 3500 RPM FOR 5 MINUTES; SWITCH TO IMPELLER MIXING; COOL TO ROOM TEMPERATURE.

The composition obtained as described in Example 1 was then filled into an airless pump container (e.g., 30 ml TopFill airless pump from MegaPlast-Mega Pumps) and then tested for physical stability (color, odor, viscosity, pH, appearance, etc.) under accelerated conditions (40 to 50° C.) for up to three months. During this period of time, the composition filled into the airless pump was stable (i.e., color, odor, viscosity, pH and appearance did not change or only changed to a limited and acceptable extent (±10% from baseline)).

The composition obtained as described in Example 1 does not leave greasy or oily residues on the skin and dries quickly and cleanly (without visible residue or significant stickiness) within one to two minutes after application on the skin.

Example 2

Additional compositions formulated in accordance with the present invention are presented in Table 20. Again, these compositions serve as illustrative formulations which provides the advantageous features of the invention, namely, mildness to the skin after application with no or only limited skin irritancy; clearness and non-greasiness upon application (transparent) to face and other skin areas other than the palms and the soles; and quick-drying, particularly when the compositions are preferably formulated as water-in-oil formulations.

TABLE 20

| NO. | PHASE | INGREDIENT (TRADE NAME) | INCI DESIGNATION | SUPPLIER | % BY WEIGHT |
|---|---|---|---|---|---|
| 1 | A | DEIONIZED WATER | WATER (AQUA) | | 59.680 |
| 2 | A | NA₂EDTA | DISODIUM EDTA | AKZO | 0.100 |
| 3 | A | KELTROL CG-T | XANTHAN GUM | CP KELCO | 0.300 |
| 4 | A | ELESTAB CPN ULTRA PURE | CHLORPHENESIN | COGNIS | 0.300 |
| 5 | A | PHENOXETOL | PHENOXYETHANOL | CLARIANT | 0.600 |
| 6 | A | SEPIWHITE MSH | UNDECYLENOYL PHENYLALANINE | SEPPIC | 0.500 |
| 7 | A | SODIUM GLYCEROPHOSPHATE (Ph. Eur. 6 Ed, Item# 500012045500) | SODIUM GLYCEROPHOSPHATE | DR. PAUL LOHMANN | 3.000 |
| 8 | A | L-LEUCINE | LEUCINE | AJINOMOTO | 1.000 |
| 9 | B | LIPOWAX D | CETEARYL ALCOHOL CETEARETH-20 | LIPO | 6.000 |
| 10 | B | LIPO GMS 450 | GLYCERYL STEARATE | LIPO | 6.000 |
| 11 | B | CERAPHYL 230 | DIISOPROPYL ADIPATE | ISP SUTTON | 3.000 |
| 12 | B | DC TORAY FZ-3196 | CAPRYLYL METHICONE | DOW CORNING | 3.000 |
| 13 | B | DC 200 FLUID 100 CST | DIMETHICONE | DOW CORNING/UNIVAR | 1.000 |
| 14 | B | LIPOVOL J | *SIMMONDSIA CHINENSIS* (JOJOBA) SEED OIL | LIPO | 1.000 |
| 15 | B | SHEA BUTTER HMP | *BUTYROSPERMUM PARKII* (SHEA BUTTER) | EARTH SUPPLIED PRODUCTS | 1.000 |
| 16 | B | VITAMIN E ACETATE OIL (USP, FCC) | DL-ALPHA TOCOPHERYL ACETATE | BASF/ CHEMCENTRAL | 0.200 |
| 17 | C | CITRIC ACID 50% SOLUTION (TO pH 4.5-5.0) | CITRIC ACID | PCI | 1.920 |
| 18 | D | EASTMAN ™ HYDROQUINONE (USP GRADE) | HYDROQUINONE | EASTMAN/ CHEMPOINT | 4.000 |
| 19 | E | SODIUM METABISULFITE (NF/FCC) | SODIUM METABISULFITE | UPI | 0.400 |
| 20 | F | GLYCERIN 99.7% (USP) | GLYCERIN | ACME-HARDESTY | 2.000 |
| 21 | F | SYMWHITE 377 | PHENYLETHYL RESORCINOL | KAH/SYMRISE | 0.500 |
| 22 | F | VITAGEN | AMINOPROPYL ASCORBYL PHOSPHATE | BASF | 0.500 |
| 23 | G | SIMULGEL INS 100 | HYDROXYETHYL ACRYLATE/SODIUM ACRYLOYLDIMETHYL TAURATE COPOLYMER ISOHEXADECANE POLYSORBATE 60 | SEPPIC | 4.000 |
| TOTAL | | | | | 100.00 |

Such compositions (e.g., Table 20) were generally prepared in a clean and sanitized stainless steel vessel, which was suitable for blending products containing hydroquinone, as described herein below:

PHASE A: DISPERSE KELTROL IN WATER, MIX UNTIL ALL HYDRATES;
  ADD EDTA, MIX UNTIL ALL DISSOLOVES;
  ADD REMAINING PHASE A INGREDIENTS, HEAT TO 75° C. WHILE MIX UNTIL ALL DISSOLVES.
PHASE B: COMBINE PHASE B INGREDIENTS, HEAT TO 75° C., MIX UNTIL ALL MELTED AND UNIFORM;

WHEN BOTH PHASE A AND PHASE B AT 75° C., ADD PHASE B INTO PHASE A WITH AGITATION MIX FOR 10 MINUTES, START COOLING TO 50° C.
PHASE C: ADJUST pH WITH PHASE C TO pH 4.5-5.0, COOL TO 45° C.
PHASE D: ADD PHASE D TO BATCH WITH MIX, MDC UNTIL ALL DISSOLVES AND UNIFORM.
PHASE E: ADD PHASE E TO BATCH WITH MIXING, MIX UNTIL ALL DISSOLVES.
PHASE F: COMBINE PHASE F INGREDIENTS, SLIGHTLY HEAT AND MIX UNTIL ALL DISSOLVES, ADD TO THE BATCH.
PHASE G: ADD PHASE G TO BATCH, MIX UNTIL UNIFORM;
  HOMOGENIZE THE BATCH AT 3500 RPM FOR 5 MINUTES, SWITCH TO IMPELLER MIXER, MIX;
  ADJUST pH WITH PHASE C TO pH 4.5-5.0 IF NECESSARY.

The composition obtained as described in Example 2 was then filled into aluminum tubes (or aluminum coated plastic tubes) and then tested for physical stability (color, odor, viscosity, pH, appearance) and chemical stability (by HPLC) of hydroquinone under accelerated conditions (40 to 50° C.) for up to three months. During this period of time, the composition filled into aluminum tubes was stable (i.e., color, odor, viscosity, pH and appearance did not change or only changed to a limited and acceptable extent (±10% from baseline) and the hydroquinone content remained between 3.84% to 4.24% (weight %).

The composition obtained as described in Example 2 does not leave greasy or oily residues on the skin and dries quickly and cleanly (without visible residue or significant stickiness) within one to two minutes after application on the skin.

Example 3

Additional compositions formulated in accordance with the present invention are presented in Table 21. These compositions serve as illustrative formulations, which provide the advantageous features of the invention, namely, stability of the composition, mildness to the skin after application with no or only limited and acceptable skin irritancy; clearness and non-greasiness upon application (transparent) to face and other skin areas other than the palms and the soles; and quick-drying, particularly when the compositions are preferably formulated as water-in-oil formulations.

CHECK pH OF BATCH; pH SHOULD BE BETWEEN 4.5-5.0
PHASE C: COMBINE PHASE C INGREDIENTS;
  HEAT TO 60° C., MIX UNTIL ALL MELTED AND UNIFORM;
  WHEN BOTH, COMBINED PHASES A & B AND PHASE C ARE AT 60° C.,
  ADD PHASE C INTO COMBINED PHASES A & B WITH AGITATION
  MIX FOR 10 MINUTES; START COOLING TO 45° C.
PHASE D: ADD PHASE D TO BATCH WITH MIX, MIX UNTIL ALL DISSOLVES AND UNIFORM.
PHASE E: ADD PHASE E TO BATCH WITH MIXING, MIX UNTIL ALL DISSOLVES.
PHASE F: COMBINE PHASE F INGREDIENTS, SLIGHTLY HEAT AND MIX UNTIL ALL DISSOLVES, ADD TO THE BATCH.
PHASE G: ADD PHASE G TO BATCH, MIX UNTIL UNIFORM;

TABLE 21

| NO. | PHASE | INGREDIENT (TRADE NAME) | INCI DESIGNATION | % BY WEIGHT |
|---|---|---|---|---|
| 1 | A | DEIONIZED WATER | WATER (AQUA) | 59.680 |
| 2 | A | NA₂EDTA | DISODIUM EDTA | 0.100 |
| 3 | A | KELTROL CG-T | XANTHAN GUM | 0.300 |
| 4 | A | ELESTAB CPN ULTRA PURE | CHLORPHENESIN | 0.300 |
| 5 | A | PHENOXETOL | PHENOXYETHANOL | 0.600 |
| 6 | A | SEPIWHITE MSH | UNDECYLENOYL PHENYLALANINE | 0.500 |
| 7 | A | SODIUM GLYCEROPHOSPHATE (Ph. Eur. 6 Ed, Item# 500012045500) | SODIUM GLYCEROPHOSPHATE | 3.000 |
| 8 | A | L-LEUCINE | LEUCINE | 1.000 |
| 9 | B | CITRIC ACID 50% SOLUTION (TO pH 4.5-5.0) | CITRIC ACID | 1.920 |
| 10 | C | LIPOWAX D | CETEARYL ALCOHOL CETEARETH-20 | 6.000 |
| 11 | C | LIPO GMS 450 | GLYCERYL STEARATE | 6.000 |
| 12 | C | CERAPHYL 230 | DIISOPROPYL ADIPATE | 3.000 |
| 13 | C | DC TORAY FZ-3196 | CAPRYLYL METHICONE | 3.000 |
| 14 | C | DC 200 FLUID 100 CST | DIMETHICONE | 1.000 |
| 15 | C | LIPOVOL J | *SIMMONDSIA CHINENSIS* (JOJOBA) SEED OIL | 1.000 |
| 16 | C | SHEA BUTTER HMP | *BUTYROSPERMUM PARKII* (SHEA BUTTER) | 1.000 |
| 17 | C | VITAMIN E ACETATE OIL (USP, FCC) | DL-ALPHA TOCOPHERYL ACETATE | 0.200 |
| 18 | D | EASTMAN ™ HYDROQUINONE (USP GRADE) | HYDROQUINONE | 4.000 |
| 19 | E | SODIUM METABISULFITE (NF/FCC) | SODIUM METABISULFITE | 0.400 |
| 20 | F | GLYCERIN 99.7% (USP) | GLYCERIN | 2.000 |
| 21 | F | SYMWHITE 377 | PHENYLETHYL RESORCINOL | 0.500 |
| 22 | F | VITAGEN | AMINOPROPYL ASCORBYL PHOSPHATE | 0.500 |
| 23 | G | SIMULGEL INS 100 | HYDROXYETHYL ACRYLATE/SODIUM ACRYLOYLDIMETHYL TAURATE COPOLYMER ISOHEXADECANE POLYSORBATE 60 | 4.000 |
| TOTAL | | | | 100.000 |

Such compositions (e.g., Table 21) were generally prepared in a clean and sanitized stainless steel vessel, which was suitable for blending products containing hydroquinone, as described herein below:

PHASE A: WEIGHT WATER AND HEAT TO 70° C.
  DISPERSE KELTROL IN WATER, MIX UNTIL ALL HYDRATES;
  ADD EDTA, MIX UNTIL ALL DISSOLVES;
  THEN ADD REMAINING PHASE A INGREDIENTS ONE BY ONE; MIX UNTIL ALL DISSOLVES.
PHASE B: ADD CITRIC ACID 50% SOLUTION TO PHASE A; MIX WELL;

HOMOGENIZE THE BATCH AT 3500 RPM FOR 5 MINUTES, SWITCH TO IMPELLER MIXER, MIX FOR 5 to 10 MINUTES; CHECK FINAL pH;
ADJUST pH WITH PHASE B TO pH 4.5-5.0 IF NECESSARY.

Compositions obtained as described in Example 3 were then filled into aluminum tubes (or aluminum coated plastic tubes) and then tested for physical stability (color, odor, viscosity, pH, appearance) and chemical stability (by HPLC; following USP protocol for hydroquinone analysis) of hydroquinone under accelerated conditions (40 to 50° C.) for up to three months. During this period of time, the composition was stable and the hydroquinone content remained between 3.84% to 4.24% (weight %).

These compositions do not leave greasy or oily residues on the skin and dries quickly and cleanly (without visible residue or significant stickiness) within one to two minutes following application on the skin.

Example 4

The results of skin tolerability testing (e.g., no or only limited and acceptable skin irritancy) of the compositions formulated in accordance with the present invention are presented below.

The compositions of the present invention can be evaluated by acute (1 day) or repetitive (more than one day) human irritancy patch test to assess the skin irritation potential. The repetitive human irritancy patch test provides "exaggerated" irritation data since the test material is applied repetitively at a rather large dose (i.e., >20 mg per cm$^2$) under occlusive (i.e., allowing no water diffusion from skin surface to air) or semi-occlusive conditions (i.e., allowing limited water diffusion from skin surface to air). Therefore, the repetitive human irritancy patch test allows easily distinguishing skin irritation (i.e., skin irritation potential) of different compositions.

The composition obtained as described in Example 3 was evaluated by repetitive human irritancy patch test over a period of three weeks (with 15 observations (i.e., evaluation of patch application sites for severity of skin irritation); one observation before patch application at beginning of study followed by 14 additional observations; see below for more details) on the back of 25 subjects. The test was performed according to standard irritancy patch testing by an independent contract organization specialized in consumer product testing. Several currently commercialized skin lightening prescription products with 4% hydroquinone were also evaluated under identical conditions for comparison. The repetitive human irritancy patch test demonstrated that the composition obtained as described in Example 3 was equally or better tolerated than a series of currently commercialized skin lightening prescription products with 4% hydroquinone. (See FIG. 1)

As shown in FIG. 1, the following compositions were evaluated:
  i) Composition described in Example 3
  ii) Composition A: composition with 4% hydroquinone and further containing sodium lauryl sulfate and lactic acid (OBAGI NU-DERM® Blender® (PM 5) by OMP Inc., Long Beach, Calif. 90802; Lots: 6K2423 and 8E1677)
  iii) Composition B: composition with 4% hydroquinone and further containing sodium lauryl sulfate and lactic acid (OBAGI-C RX SYSTEM™ C-Therapy Night Cream (PM) by OMP Inc., Long Beach, Calif. 908020; Lot: 8E1440)
  iv) Composition C: composition with 4% hydroquinone and further containing glycolic acid (LUSTRA® Hydroquinone USP 4% by Taro Pharmaceuticals U.S.A, Hawthorne, N.Y. 10532; Lot: H8114)
  v) Composition D: composition with 4% hydroquinone and further containing sodium lauryl sulfate (GLYTONE Skin Bleaching/Clarifying Cream Hydroquinone USP 4% by Pierre Fabre/Genesis Pharmaceutical Inc., Parsippany N.J. 07054; Lot: 1058/01)

The following standard method was used to assess skin irritation:

The upper back between the scapulae served as treatment area. Approximately 0.2 grams of each test material was applied to the 1 inch×1 inch absorbent pad portion of an adhesive strip. When secured to the appropriate treatment site, these dressings formed semi-occlusive patches. Each test material was applied to the appropriate treatment site Monday through Friday to maintain twenty-one (21) consecutive days of direct skin contact. Patches applied on Friday remained n place until the following Monday. Evaluations of the test sites were conducted prior to each patch application. It was noted that due to inclement weather, two of the 25 subjects were unable to report, as scheduled. They were instructed to keep their patches in place and return on the following day. If a test site had been observed to exhibit an evaluation score of a "3" or higher, the application of test material to this site would have been discontinued and the observed score of "3" (or higher) would be recorded for the remaining study days.

The following evaluation key was used: (0) no visible skin reaction; (+) barely perceptible or spotty erythema; (1) mild erythema covering most of the test site; (2) moderate erythema, possible presence of mild edema; (3) marked erythema, possible edema; (4) severe erythema, possible edema, vesiculation, bullae and/or ulceration.

Example 5

The results of color stability of the compositions formulated in accordance with the present invention are presented below. In Examples 1, 2 and 3, the color of the compositions of the present invention is described as being stable (e.g., characteristic white color of compositions does not significantly change for up to three months at elevated temperatures as evaluated visually with the naked eye) when the composition is placed (i.e., filled) into an adequate container.

In this Example, the color stability was evaluated after the composition was removed from its typical (e.g., commercialized) container such as aluminum tube, aluminum coated plastic tube, or airless pump. A pea size amount was placed onto a flat, inert, white surface (e.g., porcelain dish) and left under normal environmental conditions (i.e., temperature, light, air, etc.) of a room (i.e., living room) in a household for at least two weeks. The color of the composition was documented by standard, digital color photography at beginning and at end of the observation period. Several currently commercialized skin lightening prescription products with 4% hydroquinone were also evaluated under identical conditions for comparison.

Figure 2:
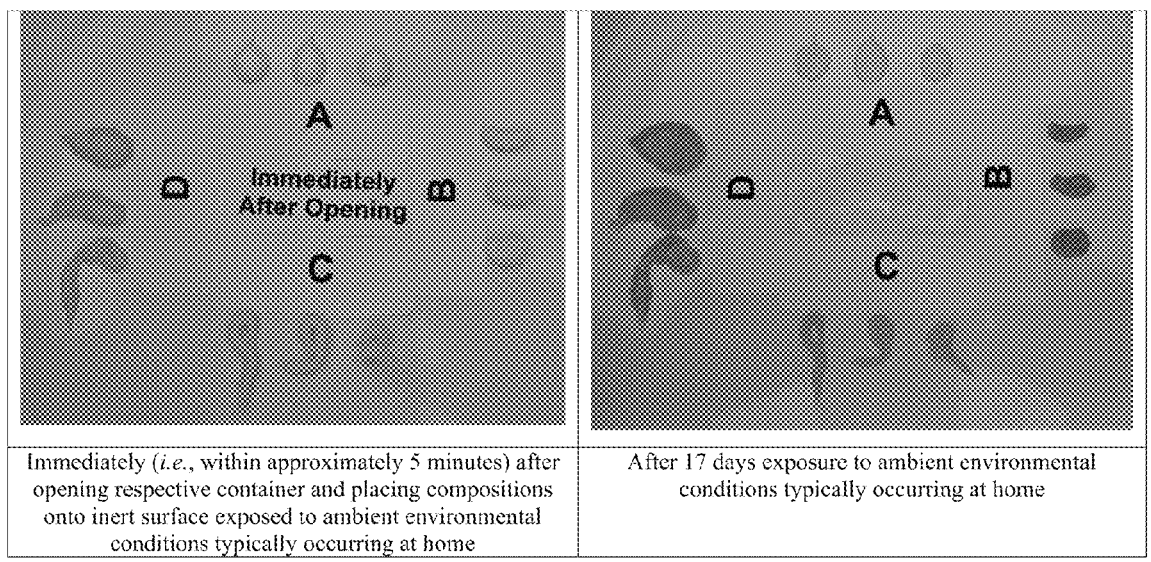
FIG. 2 shows the color stability of a composition of the present invention (Composition A) as compared to other, control compositions (e.g.: Compositions B, C and D), which are not part of this invention.

As shown in FIG. 2, the following compositions were evaluated:
  i) Composition A: composition described in Example 3
  ii) Composition B: composition with 4% hydroquinone and further containing retinol (EpiQuin® Micro by SkinMedica, Carlsbad, Calif. 92010)
  iii) Composition C: composition with 4% hydroquinone and further containing 0.01% fluocinolone acetonide and 0.05% tretinoin (Tri-Luma® Cream by Galderma Laboratories, Fort Worth, Tex. 76177)
  iv) Composition D: composition with 4% hydroquinone and further containing sodium lauryl sulfate and lactic acid (OBAGI NU-DERM® Blender® (PM 5) by OMP Inc., Long Beach, Calif. 90802)

The compositions were removed from their typical container and placed onto porcelain dish and left under normal environmental conditions (i.e., temperature, light, air, etc.) of a room (i.e., living room) in a household for 17 days. The composition of the present invention (Composition A) did not show any significant color change after 17 days as judged by photography or visually. However, Compositions B, C and D showed all significant (i.e., clearly visible) color changes (i.e., color is changing from white to brown or brownish, or becoming darker, more brownish, or darker yellow) after 17 days. These color changes became more visible with time. The color changes are mainly due to oxidation of hydroquinone, which is a constituent of Compositions B, C and D. While hydroquinone is also a constituent of Composition A, this experiment thus illustrates that the hydroquinone of Composition A is stable under the conditions of this experiment.

Although the color changes described in this Example for Composition B, C and D generally occurs when the composition is placed outside its typical container, these observed color changes are not desirable, as such color changes may affect the efficacy of the product (i.e., composition being exposed to air and light after it is applied onto skin). Furthermore, the color changes would occur after short time once some composition adheres to the outside of the container (e.g., the tube outlet or pump head) after the first and all subsequent uses of the composition. All of these factors make the composition less desirable to use, which consequently affects the patient's adherence to the recommended course of treatment (i.e., patient compliance) and therefore reduces the likelihood for an efficient treatment outcome.

Example 6

The compositions obtained as described in Examples 1, 2, and 3 were evaluated for tolerability and efficacy in treating skin pigmentation disorders, such as melasma, post-inflammatory hyperpigmentation, pigmentation changes due to skin aging, or any other skin conditions related with normal such as skin of color or abnormal pigmentation such as hypo- or hyper-pigmentation in humans. The compositions were generally applied to the affected skin area(s) either once daily in the evening (at least about half an hour before bedtime) or twice daily in the morning and in the evening. A sunscreen offering at least a sun protection factor of 15 (SPF15) (e.g., JOURNÉE Bio-restorative Day Cream by Neocutis Inc., San Francisco, Calif. 94123) was used during daytime to protect skin from sun. In case the compositions were also used at daytime, the subjects were instructed to apply the sunscreen after having applied the said compositions; preferentially at least half an hour after having applied the compositions.

The studies lasted at least three months (i.e., 12 weeks) and were continued over a longer period of time depending on severity of the skin pigmentation disorder. Epidermal melasma can be treated (i.e. skin pigmentation is visibly reduced at site of application) within about one to three months, whereas dermal melasma, mixed type melasma, post-inflammatory hyperpigmentation (e.g., hyperpigmentation originating after inflammation of skin such as related to skin burns, wounds, acne, use of certain medications, dermatitis, etc.), pigmentation changes due to skin aging (e.g., freckles, age or liver spots, etc.), or any other skin conditions related with normal such as skin of color (e.g., skin of individual with Hispanic, Asian, African or American/African origins), or abnormal pigmentation such as hypo- or hyper-pigmentation in humans may require generally at least a three month treatment period to see results (i.e. skin pigmentation is visibly reduced at site of application) when using compositions formulated in accordance with the present invention; eventually in combination with the use of a sunscreen product.

Figure 3:
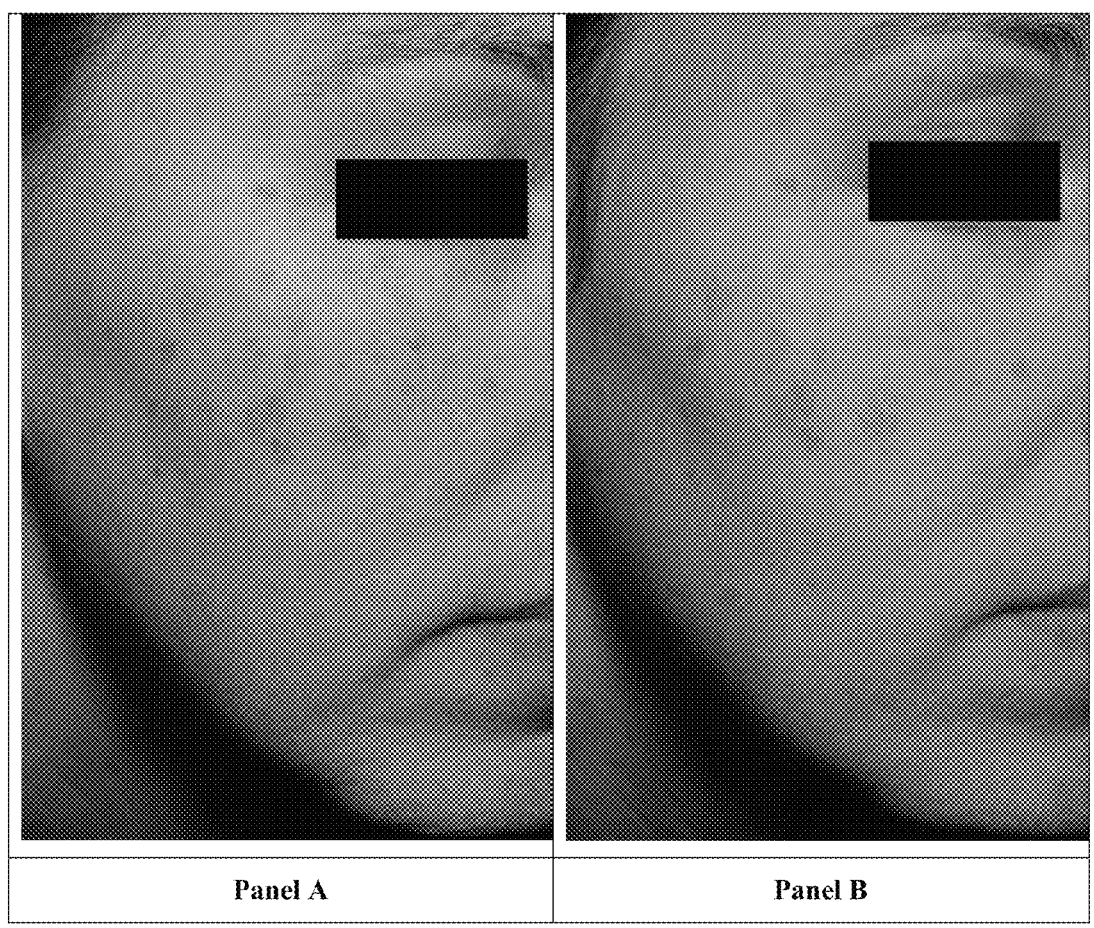
FIG. 3 is a photograph showing the reduction of pigmentation in the skin of a patient using the compounds of the present invention (i.e., the composition described in Example 3, infra). Panel A shows the hyperpigmentation of the patient's skin prior to administration of a compound of the present invention. Panel B shows the reduction in skin pigmentation following 12 weeks of treatment with a composition of the present invention.

Results demonstrating the efficacy of the compositions formulated in accordance with the present invention are presented in FIG. 3.

Study with Composition Described in Example 1:

After a one month wash-out period where the subjects were allowed to only use JOURNÉE Bio-restorative Day Cream (offering SPF30+), the subjects applied the composition described in Example 1 twice daily (morning and evening) to their entire face after washing the face with a gentle skin cleanser (i.e., NEO-CLEANSE Gentle Cleanser by Neocutis). In the morning, they continued to use JOURNÉE Bio-restorative Day Cream.

Assessment of global melasma severity was performed by the investigator according to the following 4-point visual scoring system: 0=absent (color of the melasma lesions is close to that of surrounding skin; 1=mild (color is slightly darker than that of normal skin); 2=moderate (color is moderately darker); and 3=severe (color is markedly darker than surrounding normal skin). In addition, melasma was quantified with the help of the so-called MASI index (see Arch Dermatol 130, 1994, 727-733).

Three areas of the face were evaluated: forehead (F), malar region (M), and chin (C) corresponding to 30%, 60% and 10% of total face The involvement of melasma in the area of forehead, malar region, and chin were given a numerical value ($A_F$, $A_M$, $A_C$): 0=no involvement; 1=less than 10% involvement; 2=10% to <30%; 3=30% to <50%; 4=50% to <70%; 5=70% to <90%; 6=90% to 100%. Severity was based on two factors: darkness (D) of melasma compared with normal skin; and homogeneity (H) of hyperpigmentation. Patients were assessed on a scale from 0 through to 4 as follows; the darkness (D) scale: 0=absent; 1=slight; 2=mild; 3=marked; 4=maximum; and the homogeneity (H) scale: 0=minimal; 1=slight; 2=mild; 3=marked; 4=maximum. To calculate the MASI score, the sum of the severity rating of darkness (D) and homogeneity (H) was multiplied by the numerical value of the respective areas involved (A) and by the various percentages of the three facial areas. These values were added to obtain the MASI score as follows: MASI=0.3 $(D_F+H_F)A_F+0.6(D_M+H_M)A_M+0.1(D_C+H_C)A_C$. Additionally, the number of age and liver spots were counted in face. Those evaluations were performed at the beginning of study (i.e., before wash-out period), after the one month wash-out period (i.e., before starting with the treatment with composition), and at the end of the study period (i.e., after 12 weeks of use of composition), respectively.

TABLE 22

| | Reduction in Global Melasma Severity as assessed by Investigator Global Assessment | Reduction in Melasma as assessed by MASI-Scoring | Reduction in total Number of Age/Liver Spots |
|---|---|---|---|
| After one month wash-out period | 0 ± 0% | 2 ± 3% | 0 ± 0% |
| After 12 weeks of use of composition | 20 ± 27% | 56 ± 33% | 55 ± 22% |

Table 22 shows the efficacy of the composition described in Example 1 in treating skin pigmentation disorders and diseases. The average and standard deviation in the reduction from baseline (i.e., data before wash-out) from five female subjects who completed the study is shown in percentage (%) of reduction from baseline.

This study shows that the composition leads to a reduction in melasma severity and in the number (and intensity) of age or liver spots in face. Thus, the composition is effective for treating (i.e., reducing) symptoms of skin pigmentation disorders and diseases. The composition was further well tolerated. As further shown in this study, the use of a sunscreen (i.e., JOURNEE Bio-restorative Day Cream) alone did not result in any significant reduction in symptoms of skin pigmentation disorders and diseases.

Study with Composition Described in Example 3:

The subjects applied the composition described in Example 3 once daily (evening) to either the right, or to the left side of their face (the side was randomly assigned) after washing the face with a gentle skin cleanser (i.e., Cetaphil by Galderma). In the morning, they additionally used JOURNÉE Bio-restorative Day Cream.

Assessment of global melasma severity was performed by the investigator according to the following 4-point visual scoring system: 0=absent (color of the melasma lesions is close to that of surrounding skin; 1=mild (color is slightly darker than that of normal skin); 2=moderate (color is moderately darker); and 3=severe (color is markedly darker than surrounding normal skin). In addition, melasma was quantified with the help of the so-called MASI index (Arch Dermatol 130, 1994, 727-733). Three areas of the face were evaluated: forehead (F), malar region (M), and chin (C) corresponding to 30%, 60% and 10% of total face; or 15%, 30% and 5% of half of the face, respectively. The involvement of melasma in the area of forehead, malar region, and chin were given a numerical value ($A_F$, $A_M$, $A_C$): 0=no involvement; 1=less than 10% involvement; 2=10% to <30%; 3=30% to <50%; 4=50% to <70%; 5=70% to <90%; 6=90% to 100%. Severity was based on two factors: darkness (D) of melasma compared with normal skin; and homogeneity (H) of hyperpigmentation. Patients were assessed on a scale from 0 through to 4 as follows; the darkness (D) scale: 0=absent; 1=slight; 2=mild; 3=marked; 4=maximum; and the homogeneity (H) scale: 0=minimal; 1=slight; 2=mild; 3=marked; 4=maximum. To calculate the MASI score for a half-face ($MASI_{Half-Face}$), the sum of the severity rating of darkness (D) and homogeneity (H) was multiplied by the numerical value of the respective areas involved (A) and by the various percentages of the three facial areas. These values were added to obtain the MASI score as follows: $MASI=0.15(D_F+H_F)A_F+0.3(D_M+H_M)A_M+0.05(D_C+H_C)A_C$. Those evaluations were performed at the beginning of study (i.e., before starting with the treatment with composition), and at the end of the study period (i.e., after 12 weeks of use of composition), respectively.

TABLE 23

| | Reduction in Global Melasma Severity as assessed by Investigator Global Assessment | Reduction in Melasma as assessed by MASI-Scoring |
|---|---|---|
| After 12 weeks of use of composition | 38 ± 37% | 74 ± 20% |

Table 23 shows the efficacy of the composition described in Example 3 in treating skin pigmentation disorders and diseases. The average and standard deviation in the reduction from baseline (i.e., data before starting with the treatment with composition) from ten female subjects who completed the study is shown in percentage (%) of reduction from baseline.

FIG. 3 is a photograph showing the reduction of pigmentation in the skin of a patient using the compounds of the present invention (e.g. the composition described in Example 3). Panel A shows the hyperpigmentation of the patient's skin prior to administration of a compound of the present invention. Panel B shows the reduction in skin pigmentation following 12 weeks of treatment with a composition of the present invention.

The results of this study show that the composition leads to a reduction in melasma severity in treated area of face. Thus, the composition is effective for treating (i.e., reducing) symptoms of skin pigmentation disorders and diseases. The composition was further well tolerated.

Study with Composition Described in Example 2:

As shown in diverse in use studies, the composition obtained as described in Example 2 was also shown to be well tolerated and efficient in treating skin pigmentation disorders, such as melasma, post-inflammatory hyperpigmentation, pigmentation changes due to skin aging, or any other skin conditions related with normal such as skin of color or abnormal pigmentation such as hypo- or hyper-pigmentation in humans. Female and male human subjects were included in this study.

These studies demonstrated that the compositions obtained as described in Examples 1, 2 and 3 are effective for treating (i.e., reducing) symptoms of skin pigmentation disorders and diseases and are well tolerated under in use conditions.

Example 7

A human study showed that the composition described in Example 3 does not cause an acnegenic/comedogenic response. Thus, the use of this composition did not result in a significant increase in the number and severity of comedones/acne.

Prior to initiation of the study, each subject was examined and the facial skin condition, including counts of non-inflammatory and inflammatory lesions, were recorded. Severity of comedones/acne were determined by the following lesion count categories:

Grade I (mild)=Less than 10 comedones (including open: blackheads; closed: micropapules and whiteheads and/or inflammatory papulopustular lesions on one or both sides of the face.

Grade II (moderate)=10-25 comedones (including open: blackheads; closed: micropapules and whiteheads) and/or inflammatory papulopustular lesions on one or both sides of the face.

Grade III (severe)=More than 25 comedones (including open: blackheads; closed: micropapules and whiteheads) and/or inflammatory papulopustular lesions on one or both sides of the face.

Subjects were evaluated before and after four weeks of treatment (once daily in evening) with the composition. Differences between baseline and final dermatological evaluations were considered statistically significant, if the probability of obtaining the result by chance is less than or equal to 0.05 using analysis of variance and/or appropriate t-Test statistics. All assessments of facial skin condition and lesion counts were made by a Board Certified Dermatologist. The study was performed by an independent clinical research organization.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A non-irritating and stable composition substantially free of calcium for treating or ameliorating at least one symptom of a skin pigmentation disorder or condition comprising glycerophosphoric acid or a non-calcium salt thereof, undecylenoyl phenylalanine, phenylethyl resorcinol (4-(1-phenylethyl)1,3-benzenediol and/or L-leucine, wherein the glycerophosphoric acid or a non-calcium salt thereof is present in an amount of about 3% by weight.

2. The composition of claim 1, wherein the non-calcium salt of glycerophosphoric acid is sodium glycerophosphate.

3. The composition of claim 1, wherein the sodium glycerophosphate is present in an amount of about 3% by weight.

4. The composition of claim 1, wherein the composition further comprises at least one additional agent that modulates or regulates at least one step of melanogenesis.

5. The composition of claim 4, wherein the at least one additional agent is selected from the group consisting of L-alanine, glycine, L-isoleucine, hydroquinone, arbutin, bearberry leaf extract, kojic acid, oxyresveratrol, gnetol, a melanosome transfer inhibitor, and an α-MSH antagonist.

6. The composition of claim 1, wherein the composition further comprises at least one skin moisturization and skin rejuvenation agent.

7. The composition of claim 6, wherein the skin moisturization and skin rejuvenation agent is selected from the group consisting of ascorbic acid, vitamin E, jojoba oil, shea butter, human fibroblast lysate, retinoic acid, retinol, and any derivatives thereof.

8. The composition of claim 1, wherein said composition is suitable for topical administration to a subject in need thereof.

9. The composition of claim 1, wherein said composition is a topical formulation in the form of a solution, an oil-in-water emulsion, a water-in-oil emulsion, a gel, an ointment, a patch, a paste, a liquid, a foam, a mousse, a spray, an aerosol, a triple emulsion, a nanoemulsion, a microemulsion, a hydrogel, a jelly, a dispersion, a suspension, and a tape.

10. The composition of claim 1, wherein said composition is stable, does not cause an acnegenic or comedogenic response, and produces minimal skin irritation in said subject.

11. A method of treating or ameliorating a skin pigmentation disorder comprising topically administering an effective amount of the composition of claim 1 to a patient suffering therefrom.

12. The method of claim 11, wherein the skin pigmentation disorder is selected from the group consisting of melasma, post-inflammatory hyper-pigmentation, pigmentation changes due to skin aging, age or liver spots, freckles, hypo-pigmentation, and hyper-pigmentation.

13. The method of claim 11, wherein the patient is a human.

14. The method of claim 11, wherein, following administration, the composition reduced skin pigmentation in the patient.

15. A pharmaceutical formulation comprising the composition of claim 1 and at least one pharmaceutically acceptable carrier.

16. A cosmetic formulation comprising the composition of claim 1 and at least one cosmetically acceptable carrier.

17. A kit comprising, in one or more containers, the pharmaceutical formulation of claim 15.

18. A kit comprising, in one or more containers, the cosmetic formulation of claim 16.

19. The kit of claim 17 further comprising instructions for use of the pharmaceutical formulation in the treatment or amelioration of said skin pigmentation disorder or condition.

20. The kit of claim 18 further comprising instructions for use of the cosmetic formulation in the treatment or amelioration of said skin pigmentation disorder or condition.

21. A unit dosage form comprising a therapeutically effective amount of the composition of claim 1.

22. A method of reducing skin pigmentation in a patient comprising topically administering an effective amount of the composition of claim 1 to the patient.

23. The composition of claim 1, wherein the composition further comprises an antioxidant.

* * * * *